United States Patent [19]

Baschang et al.

[11] 4,409,209
[45] Oct. 11, 1983

[54] NOVEL PHOSPHORYLMURAMYL PEPTIDES AND PROCESSES FOR THE MANUFACTURE THEREOF

[75] Inventors: Gerhard Baschang, Bettingen, Switzerland; Lajos Tarcsay, Grenzach-Wyhlen; Albert Hartmann, Grenzach, both of Fed. Rep. of Germany; Jaroslav Stanek, Birsfelden, Switzerland

[73] Assignee: Ciba-Geigy Corporation, Ardsley, N.Y.

[21] Appl. No.: 327,381

[22] Filed: Dec. 4, 1981

Related U.S. Application Data

[62] Division of Ser. No. 194,104, Oct. 6, 1980, Pat. No. 4,323,560.

[51] Int. Cl.³ .............................................. A61K 37/00
[52] U.S. Cl. .................................................... 424/177
[58] Field of Search .................. 260/112.5 R; 424/177

[56] References Cited

U.S. PATENT DOCUMENTS

| | | | |
|---|---|---|---|
| 4,082,735 | 4/1978 | Jones et al. | 260/112.5 R |
| 4,082,736 | 4/1978 | Jones et al. | 260/112.5 R |
| 4,153,684 | 5/1979 | Audibert et al. | 260/112.5 R |
| 4,323,560 | 4/1982 | Baschang et al. | 260/112.5 R |

FOREIGN PATENT DOCUMENTS

| | | | |
|---|---|---|---|
| 4512 | 10/1979 | European Pat. Off. | 260/112.5 R |
| 1570625 | 7/1980 | United Kingdom | 260/112.5 R |

*Primary Examiner*—Delbert R. Phillips
*Attorney, Agent, or Firm*—Irving N. Feit

[57] ABSTRACT

Phosphorylmuramyl peptides of the formula

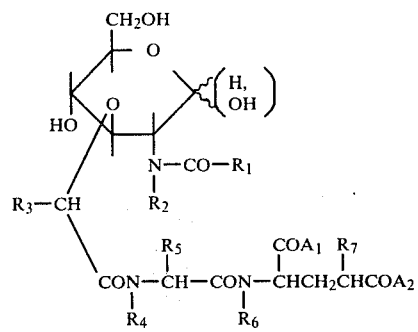

are immuno-potentiating. In the formula, $R_1$ represents optionally substituted alkyl or aryl, $R_2$, $R_4$, $R_6$ and $R_7$ represent, for example, hydrogen, $R_3$ represents hydrogen or lower alkyl, $R_5$ represents, for example, hydrogen, lower alkyl, hydroxy-lower alkyl, amino-lower alkyl, cycloalkyl, cycloalkyl-lower alkyl, aryl or aralkyl, or nitrogen-containing heterocyclyl or heterocyclyl-lower alkyl, and one of the radicals $A_1$ and $A_2$ represents a radical of the formula (II)

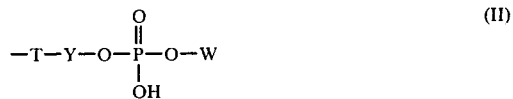

(II)

In the formula (II), T represents NH or O, Y represents an optionally substituted alkylene group, which may also be interrupted by one or two oxycarbonyl and/or iminocarbonyl groups, and W represents an aliphatic radical or a cycloalkyl or cycloalkenyl radical having more than 6 carbon atoms. The other of the radicals $A_1$ and $A_2$ represents free or etherified hydroxy, amino, lower alkylamino or aminocarbonyl-lower alkylamino.

27 Claims, No Drawings

NOVEL PHOSPHORYLMURAMYL PEPTIDES AND PROCESSES FOR THE MANUFACTURE THEREOF

This is a divisional of application Ser. No. 194,104 filed on Oct. 6, 1980, now U.S. Pat. No. 4,323,560 issued Apr. 6, 1982.

The invention relates to novel phosphorylmuramyl peptides, to processes for the manufacture thereof, and to pharmaceutical preparations that contain these phosphorylmuramyl peptides, as well as to their use for stimulating immunity.

The invention relates especially to compounds of the formula

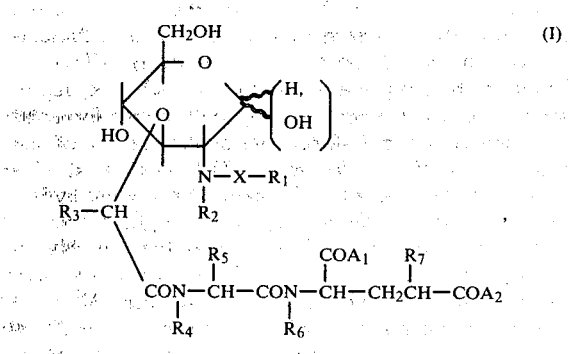

in which

X represents carbonyl or carbonyloxy, $R_1$ represents optionally substituted alkyl or aryl, $R_2$, $R_4$ and $R_6$ represent hydrogen or lower alkyl, $R_3$ represents hydrogen or lower alkyl, $R_5$ represents hydrogen, lower alkyl, free or functionally modified hydroxy-lower alkyl, free or functionally modified mercapto-lower alkyl, optionally substituted amino-lower alkyl, cycloalkyl, cycloalkyl-lower alkyl, optionally substituted aryl or aralkyl, or nitrogen-containing heterocyclyl or heterocyclyl-lower alkyl, or $R_4$ and $R_5$ together alternatively represent alkylene having 3 or 4 carbon atoms, $R_7$ represents hydrogen or optionally esterified or amidated carboxyl, and one of the radicals $A_1$ and $A_2$ represents a radical of the formula

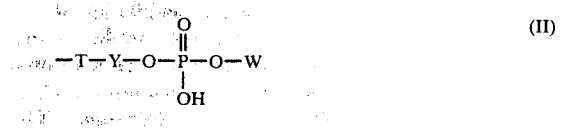

in which

T represents NH or O,

Y represents an optionally substituted alkylene group which may also be interrupted by one or two oxycarbonyl and/or iminocarbonyl groups, and W represents an aliphatic radical or a cycloalkyl or cycloalkenyl radical each having more than 6 carbon atoms and the other of the radicals $A_1$ and $A_2$ represents free or etherified hydroxy, amino or lower alkylamino, or represents aminocarbonyl-lower alkylamino optionally substituted in the lower alkyl radical, and the salts of these compounds.

Alkyl is straight-chain or branched alkyl having up to 18 carbon atoms and bonded in any position, but is especially lower alkyl.

Substituents of the optionally substituted alkyl groups are especially free or functionally modified hydroxy or mercapto groups, such as etherified or esterified hydroxy or mercapto groups, for example lower alkoxy or lower alkylthio groups, or halogen atoms or free or functionally modified carboxyl such as lower alkoxycarbonyl or carbamoyl groups. The substituted alkyl radical, such as the lower alkyl radical, may carry one, two or more identical or different substituents, especially free hydroxy groups or halogen atoms.

The aliphatic radical W is an alkyl or alkenyl radical that contains up to 30 carbon atoms and may carry as substituents preferably free or functionally modified hydroxy groups, such as etherified or esterified hydroxy groups, for example lower alkoxy or lower alkanoyloxy groups, halogen atoms or free or acylated amino groups, for example alkanoylamino, such as lower alkanoylamino, groups, or keto groups. These substituents are especially in the 2-position, that is to say in the β-position, to the phosphoryloxy group. W may alternatively represent a cycloalkyl or cycloalkenyl radical, for example cholesteryl, having up to 30 carbon atoms.

Aryl radicals are especially monocyclic and also bicyclic aryl radicals, especially phenyl, but also naphthyl. They may optionally be mono, di- or poly-substituted, for example by lower alkyl groups, by free, esterified or etherified hydroxy, for example lower alkoxy or lower alkylenedioxy, or by halogen atoms, and/or by trifluoromethyl groups.

Aralkyl is especially aryl-lower alkyl, in which aryl has the meaning given above. Aryl-lower alkyl is especially benzyl or phenylethyl, in which the phenyl nucleus may be mono-, di- or poly-substituted.

Optionally substituted aralkyl radicals are especially those radicals that, in the aromatic nucleus, are optionally mono-, di- or poly-substituted, for example by lower alkyl, by free, etherified or esterified hydroxy or mercapto groups, for example lower alkoxy or lower alkylenedioxy, and also by lower alkylthio or trifluoromethyl groups and/or by halogen atoms.

Cycloalkyl is especially cycloalkyl having 5 or 6 carbon atoms, such as cyclopentyl or cyclohexyl, and cycloalkyl-lower alkyl is especially one in which the cycloalkyl radical has 5 or 6 carbon atoms and the lower alkyl radical is especially methyl or ethyl.

Nitrogen-containing heterocyclyl is especially the radical or a 5- or 6-membered heterocyclic compound containing one or two nitrogen atoms in the ring. It may be unsaturated or saturated, and contain, for example, a fused phenyl radical. Pyrrolyl, indolyl, pyridyl and imidazolyl radicals may be mentioned as examples thereof.

In nitrogen-containing heterocyclyl-lower alkyl, the heterocyclyl radical has the meaning mentioned above and the lower alkyl radical is especially methyl or ethyl.

The alkylene radical, which may be formed by the radicals $R_4$ and $R_5$, is preferably unsubstituted and is especially the trimethylene radical.

An optionally esterified or amidated carboxyl group is especially the carboxyl group itself, or a carboxyl group esterified by a lower alkanol, or alternatively a carbamoyl group which, at the nitrogen atom, is unsubstituted or mono- or di-substituted by optionally substituted alkyl, especially lower alkyl, aryl, especially phenyl, or aralkyl, such as benzyl. Alternatively, however, the carbamoyl group may carry an alkylene radical, such as the tetra- or pentamethylene radical.

Optionally functionally modified hydroxy or mercapto groups are especially etherified or esterified hydroxy or mercapto groups, such as lower alkoxy, lower acyloxy, for example lower alkanoyloxy, or halogen atoms, lower alkylthio or lower acylthio, for example lower alkanoylthio.

Functionally modified amino-lower alkyl is especially mono- or di-lower alkylamino-lower alkyl, such as methylamino-, ethylamino-, dimethylamino- or diethylamino-lower alkyl, or acylated amino-lower alkyl, such as alkanoylamino-lower alkyl, for example lower alkanoylamino-lower alkyl.

An aminocarbonyl-lower alkylamino group optionally substituted in the lower alkyl radical is especially a lower alkylamino group that carries the aminocarbonyl radical in the 1-position, for example aminocarbonylmethylamino, 1-aminocarbonylethylamino, 1-aminocarbonylisobutylamino or 1-aminocarbonyl-3-methylbutylamino, or alternatively a 1-aminocaarbonyl-lower alkylamino group of which the lower alkyl group carries hydroxy, carboxy or amino groups, for example 1-aminocarbonyl-2-hydroxyethylamino, 1-aminocarbonyl-2-hydroxypropylamino, 1,2-bis-(aminocarbonyl)ethylamino or 1-aminocarbonyl-5-amino-1-pentylamino.

The alkylene radical Y is especially a lower alkylene radical interrupted by one or two oxycarbonyl or N-R$_8$-carbonylimino groups and is then especially a radical of the formula

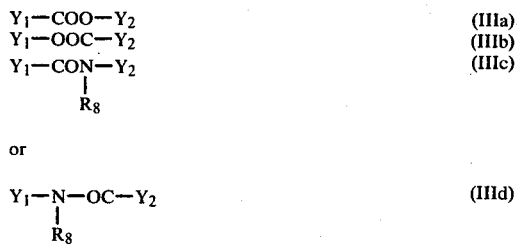

in which one of the radicals $Y_1$ and $Y_2$ represents an optionally substituted lower alkylene radical, and the other represents an optionally substituted lower alkylene radical which may also be interrupted by oxycarbonyl or N-R$_8$-carbonylamino, and $Y_1$ and $Y_2$ together have more than 2 carbon atoms, and R$_8$ represents hydrogen or lower alkyl. Substituents of the radicals $Y_1$ and $Y_2$ that should be given special mention are free or functionally modified hydroxy or hydroxy-lower alkyl, free or functionally modified mercapto or mercapto-lower alkyl, free or mono- or di-lower-alkylated or acylated amino-lower alkyl, aminocarbonyl, alkyl, cycloalkyl having 5 or ≠carbon atoms, aryl or aralkyl, wherein the general terms may have the meanings given above. The alkylene radical Y may, however, alternatively be a lower alkylene radical preferably having 2 or 3 carbon atoms.

The radicals and compounds defined by "lower" in the context of this description and the patent claims contain preferably up to and including 7, and especially up to and including 4, carbon atoms.

Hereinbefore and hereinafter the general terms may have the following meanings:

Lower alkyl is, for example, n-propyl, n-butyl, isobutyl, sec.-butyl or tert.-butyl, also n-pentyl, n-hexyl, isohexyl or n-heptyl and, especially, methyl or ethyl. In aryl-, cycloalkyl- or heterocyclyl-lower alkyl, the lower alkyl radical is especially methyl or ethyl, the aryl, cycloalkyl or heterocyclyl radical having the above-mentioned meaning.

Lower alkoxy is, for example, n-propoxy, n-butoxy, isobutoxy, sec.-butoxy or tert.-butoxy and, especially, methoxy or ethoxy.

Lower alkylthio is, for example, n-propylthio, n-butylthio, isobutylthio, sec.-butylthio or tert.-butylthio and, especially, methylthio or ethylthio.

Lower alkylenedioxy is especially methylenedioxy, ethylenedioxy or propylenedioxy.

Halogen represents fluorine or bromine, but preferably chlorine.

Lower alkanoyl is especially propionyl or butyryl, but more especially acetyl.

The compounds of the formula I may exist in the form of mixtures of isomers or as pure isomers. Preferably the radical of the formula —CH(R$_3$)—C(=O)— linked to the oxygen atom, in the case when R$_3$ represents lower alkyl, is present in optically active form and has especially the D-form, whilst the radical of the amino acid of the formula —N(R$_4$)—CH(R$_5$)—C(=O)—, in the case when R$_5$ does not represent hydrogen, is likewise preferably present in optically active form, especially in the L-form, and the terminal α-aminoglutaric acid radical is preferably present in optically active form, especially in the D-form. Also, the optionally substituted 1-hydroxy group may have the α- or β-configuration; the novel compounds of the formula I may, however, alternatively be present in the form of a mixture of 1α- and 1β-isomers.

In the compounds of the formula I the proton bonded to phosphorus by an oxygen atom can readily be split off by bases. Usually the compounds of the formula I are present in the form of a mixture of the free compounds and their salts. Of the muramyl peptides of the formula I described in the Examples, for example, approximately 40 to 55% is in the form of the sodium salt. The invention relates also to these salts.

The invention relates generally also to the salts of compounds of the formula I with any other salt-forming groups. Salt-forming groups that come into consideration are, for example, carboxyl groups that may be represented, for example, by the radicals COA$_1$, COA$_2$ or R$_7$, or amino groups in the radical R$_5$. The invention relates especially to pharmaceutically acceptable, non-toxic salts of the compounds of the formula I. Counterions of carboxylate anions to be given special mention are metal or ammonium ions, such as alkali metal and alkaline earth metal ions, for example sodium, potassium, magnesium or calcium ions, as well as ammonium ions from ammonia or suitable organic amines, such as lower alkylamines, for example triethylamine. The compounds of the formula I with basic groups, for example amino groups, can form acid addition salts. The compounds can preferably alternatively be present in the form of inner salts, that is to say, zwitterions. The proton bonded to phosphorus by an oxygen atom can, for example, protonate an amino group in the radical R$_5$. For isolation or purification, pharmaceutically unacceptable salts may also be used. Only the pharmaceutically acceptable, non-toxic salts can be used therapeutically, and are therefore preferred.

The novel phosphorylmuramyl peptides of the present invention have a number of valuable pharmacological properties, especially a pronounced immunopotentiating action.

Thus, in vivo these compounds considerably increase the ability of mice to form antibodies:

NMRI mice are immunised by intraperitoneal injection of 10 μg of precipitate-free bovine-serum-albumin (BSA) on day 0. 9, 15 and 29 days later, serum samples are taken and examined for their content of anti-BSA antibodies using a passive haemagglutination technique. In the dose used, soluble BSA is sub-immunogenic for the recipient animals, that is to say, it is unable to initiate any, or is able to initiate only a very insignificant production of antibodies. Additional treatment of the mice with certain immunopotentiating substances before or after the administration of antigen leads to an increase in the antibody titre in the serum. The effect of the treatment is expressed by the score value achieved, that is to say, by the sum of $\log_2$ titre differences on the three days on which blood samples were taken.

In this test, on intraperitoneal or subcutaneous administration of from 0.5 to 5 mg/kg animal on five successive days after immunisation with BSA, the compounds of the formula (I) are able significantly to increase the antibody production against BSA. In this respect they are greatly superior to the conventional hydrophilic muramyl peptides.

Manifestations of the cell-imparted immunity can also be potentiated in vivo by the mentioned compounds:

Whereas sensitisation of guinea pigs with BSA in incomplete Freund's adjuvant results only in humoral formation of antibodies, the admixture of the phosphorylmuramyl peptides according to the invention in a dose range of from 5 to 50 μg to the antigen-oil emulsion induces delayed hypersensitivity to BSA: three weeks after immunisation, intracutaneous injection of BSA in these animals results in a local inflammation with erythemia and thickening of the skin, which reaches its maximum within 24 to 48 hours. These delayed reactions correspond quantitatively and qualitatively to those that are normally obtained by immunisation with BSA in complete Freund's adjuvant (that is, with the addition of mycobacteria). The $ED_{50}$ values (μg/animal required for the induction of a difference in the reaction volume of 200 μl, (erythemia area × increase in skin thickness) in treated and untreated animals 24 hours after induction) are from 10 to 20 μg.

Deserving of particular emphasis is also the ability of such phosphorylmuramyl peptides, by administration together with BSA in liposomes (egg lecithin:cholesterol 4:1; 4 mg/animal) and without the toxic mineral oil component, to induce in guinea pigs a delayed hypersensitivity to BSA. Quantitatively and qualitatively these delayed reactions are likewise identical to those that are obtained by immunisation with BSA in complete Freund's adjuvant. The $ED_{50}$ values are 100 to 300 μg per animal.

Compared with hydrophilic muramyl dipeptides, the new compounds of the formula (I) have other additional improvements in quality:

Balb/c mice are immunised by intraperitoneal injection of $2 \times 10^4$ p815 mastocytoma cells on day 0. On day 15 the splenocytes of the animals immunised in this manner are examined in vitro for the presence of cytotoxic T-lymphocytes directed against P815 mastocytoma cells. For this purpose, the P815 target cells are labelled with $^{51}Cr$ and the extent of the cytotoxic reaction is ascertained by measuring the radioactivity in the culture supernatant. In the dose used, the P815 mastocytoma cells are sub-immunogenic for the recipient mice, that is to say, they induce no, or only a very insignificant, formation of cytotoxic T-cells. Simultaneous intraperitoneal administration of from 1 to 50 μg of the mentioned muramyl peptides of the formula I leads to a significant increase in the formation of cytotoxic T-cells (by a factor of 10 to 30 compared with untreated mice).

The immunopotentiating properties of the novel compounds of the formula (I) can also be demonstrated in the mouse in the case of the induction of specific immunotolerance to transplant antigens by immunisation with autoblasts to which an adjuvant has been added:

In a mixed lymphocyte culture, splenolymphocytes of the prospective tranplant recipient (C57 B1/6J mice) are incubated with irradiated splenocytes of the prospective transplant donor (CBA/J mice). T-lymphocytes having specific receptors for the histocompatibility antigens of the donor proliferate and become blast cells; these can be separated from the other cells by sedimentation. The specific blast cells express the relevant idiotypic specificities of the membrane receptors and, admixed with complete Freund's adjuvant (CFA), are injected into the prospective transplant recipients (C57 B1/6J) as autoimmunogens for the induction of specific tolerance to the relevant transplant antigens. The immunisation is carried out four times at intervals of four weeks with autologous anti-CBA/J T-lymphoblasts. Adsorbates of T-autoblasts with the novel compounds of the formula (I) ($10^9$ blast cells are suspended in a solution of 20 mg of substance in 20 ml of PBS; after a two-hour incubation period the cells are centrifuged and washed twice with PBS) are able to induce specific immunotolerance in the absence of CFA, the adsorbates being as effective as the lymphoblasts in CFA.

The novel compounds of the formula (I) are also able, in concentrations of from 0.5 to 100 μg/ml in splenocyte cultures of normal mice, to induce the formation of antibody-producing cells (an increase in the 19S-plaque-forming cells by a factor of 10 to 30 above the control value [in the absence of the stimulating substances]): thus in the presence of the mentioned compounds, for example specific antibodies against sheep erythrocytes are formed, without sheep erythrocytes being added to the cultures for the immunisation. On the other hand, when compared with a normally thymus-dependent antigen (sheep erythrocytes), the mentioned substances, in the same concentration range, are also able to increase the immunological reactivity of T-cell-depleted splenocyte cultures (of congenitally athymic nu/nu mice) (by a factor of 10 to 30 compared with untreated control cultures). The mentioned compounds, however, in vitro directly or indirectly induce not only proliferation and synthesis of β-lymphocytes (i.e. of potential antibody-forming cells), but also impart effects to T-lymphocytes (to which regulatory active promotor and suppressor cells and also cytotoxic effector cells belong). Thus, for example, the mentioned compounds in a concentration range of from 1 to 20 μg/ml are able to potentiate considerably (up to 10 times) the reactivity of cortisone-resistant thymus cells compared with allogenic irradiated stimulator lymphocytes.

The above-mentioned effects are probably indirectly brought about as a result of the fact that such phosphorylmuramyl peptides activate macrophages, which in turn promote the reactivity of T- and B-lymphocytes. In fact, it can be shown that the mentioned compounds, even in small concentrations (0.5 to 10 μg/ml), liberate large amounts of "colony stimulating activity" (CSA) from mouse-macrophages (induction of up to 150 to 200 colonies within 7 days from $10^5$ bone marrow cells of mice after the addition of 20% supernatant liquor from macrophase cultures incubated for 24 hours with the substance, compared with 0 to 5 colonies on the addition of supernatant liquors of untreated macrophage cultures). CSA is a biological mediator which is necessary for the differentiation of bone marrow parent cells from macrophages and polymorphonuclear leucocytes. The mentioned compounds in this way cause an increased supply of cells that are of prime importance for non-specific resistance and for the induction, amplification and expression of specific (lymphocyte-induced) immuno-reactions.

The immunopotentiating action of the novel compounds can be demonstrated in vivo: the injection of a phospholipid derivative of a muramyl peptide according to the invention leads within 3 to 9 hours to a great increase in the CSA concentration in the serum (up to 120 colonies per $10^5$ bone marrow cells of mice after the addition of serum extracted with chloroform [5% final concentration] compared with 0 to 5 colonies in untreated animals). Correspondingly, by administration of the same compounds in vivo the ability of mice to form antibodies is considerably potentiated.

The immunopotentiating properties of the novel compounds of the formula I can also be demonstrated in tumour models, for example the Ehrlich ascites tumor in the mouse.

An intraperitoneal injection of $10^6$ syngenic Ehrlich ascites tumor cells in Balb/c mice leads on average in 18 days to the death of the animals. If the mice are injected intraperitoneally with $10^7$ (group 1), $10^6$ (group 2) and $10^5$ (group 3) ascites tumour cells which have been charged in vitro with the novel compounds of the formula I ($10^9$ ascites tumour cells are suspended in a solution of 40 mg of the test substance in 20 ml of phosphate-buffered physiological common salt solution (PBS) and after a two-hour incubation at 37° C. the cells are centrifuged and washed twice with PBS; the cells incorporate the test compound into their membrane during this treatment) then in 18 days no tumour growth has occurred. On the 19th day, $10^6$ native Ehrlich ascites tumour cells are administered intraperitoneally to each of the animals. The following effects are observed:

group 1: 8 of the 10 animals survive the 80th day,
group 2: 6 of the 10 animals survive the 80th day,
group 3: the animals die, like the control animals, after 18 days.

The compounds according to the present invention are additionally of low toxicity: even intraperitoneal administration five times at a dose of 100 mg/kg/day on five successive days were tolerated by the mice apparently without symptoms. Because the doses required for immunostimulation are very small, the therapeutic scope of the novel compounds is very large.

The novel compounds according to the present invention can thus considerably increase the cellular and especially the humoral immunity, both in admixture with the antigen itself (adjuvant effect in the narrower sense) and when administered separately at a different time and at a different site from the antigen injection (systemic immunopotentiation).

The novel compounds according to the present invention may thus be used as adjuvants in admixture with vaccines to improve the success of vaccination and to improve the protection against infection imparted by humoral antibodies and/or cellular immunity against bacterial, viral or parasitic causative organisms.

Finally, the described compounds in admixture with various antigens are suitable as adjuvants in the experimental and industrial manufacture of antisera for therapy and diagnostics and in the induction of immunologically activated lymphocyte populations for cell transfer processes.

Moreover, the novel compounds can also be used, without simultaneous administration of antigens, to promote immune reactions in humans and animals that are already progressing subliminally. The compounds are accordingly particularly suitable for stimulating the body's defence mechanism, for example in the case of chronic and acute infections or in the case of selective (antigen-specific) immunological defects, and in hereditary and also in acquired general (i.e. not antigen-specific) immunological defective conditions, such as occur in old age, in the course of serious primary diseases and especially after therapy with ionising radiation or with hormones having an immunosuppressive action. The mentioned substances can thus be administered preferably also in combination with antibiotics, chemotherapeutic agents, or other medicines. Finally, the described substances are also suitable for general prophylaxis of infectious diseases in humans and animals.

The invention relates also to the combination of the muramyl peptides according to the invention with antibiotic agents, which causes an increase in the antibiotic activity. For this purpose an effective or under-effective dose of the antibiotic is used, depending on the nature of the latter, for example from approximately 20 to approximately 750 mg per individual dose.

The muramyl peptides of the formula I are used in individual doses of approximately 5 mg to approximately half the amount of the antibiotic. The muramyl peptide derivative can be administered up to 24 hours before or after the antibiotic, but is preferably administered at about the same time as the antibiotic.

The antibiotics are administered in the usual manner, such as subcutaneously, intravenously or orally, whilst the muramyl peptides, especially if they are administered separately from the antibiotics, are usually administered subcutaneously.

In this method, individual antibiotics, as well an antibiotic mixtures, may be used. Antibiotic preparations which are characterised in that they contain one or more of the afore-mentioned antibiotics and at least one muramyl peptide of the formula I contain the usual amounts of antibiotics, for example between 20 and 1000 mg, preferably between approximately 200 and 500 mg, and 5 mg up to half the amount of the antibiotic of muramyl peptide of the formula I. Especially when these preparations are to be administered orally, they may also contain the usual amounts of pharmacological carriers, extenders and/or diluents.

The high antibiotic effect of the new process and the new preparations can be exhibited by "in vivo" tests which are carried out on various types of animals, especially mammals, such as mice. For this purpose, the animals are infected with a lethal or sub-lethal dose of a pathogenic microorganism and then the said new preparation, or the individual doses of muramyl peptide and antibiotic, are administered. The effect is ascertained as $ED_{50}$, which is that dose at which 50% of the animals survive.

It has now surprisingly been found that the infection by pathogenic bacilli, especially of gram-negative bacteria which are more difficult to influence, such as, for example, strains of Aerobacter, Brucella, Escherichia, Klebsiella, Malleomyces, Neisseria, Pasteurella, Proteus, Pseudomonas, Shigella and Vibro, but also of gram-positive bacteria, such as Actinomycetes, Clostridia, Corynebacteria, Diplococci, Mycobacteria or Staphylococci, or of fungi, such as *Candida albicans, Cryptococcus neoformans, Plastomyces dermatitides* or *Hystoplasma capsulatum*, is inhibited and combated to an increased extent.

Of the antibiotics suitable for combination with the muramyl peptides according to the invention, especially those from the following groups may be mentioned: β-lactam antibiotics, aminoglycosides, tetracyclines, macrolides, lincomycins, polyene antibiotics, polypeptide antibiotics, anthracyclines, chloramphenicols, thiamphenicols, cycloserines, fusidic acids or rifamycins.

Penicillins, cephalosporins, penems, nocardicines, thienamycins and clavulanic acids may be mentioned as the preferred antibiotics of the β-lactams.

Penicillin antibiotics are especially amoxycillin, ampicillin, carbenicillin, cloxacillin, cyclacillin, dicloxacillin, mecillinam, methicillin, penicillin G, penicillin V, pivampicillin, sulbenicillin, azlocillin, ticarcillin, mezlocillin, pivmecillinam or 6-(4-endoazatricyclo[5.2.2.0$^{2,6}$]undec-8-enyl)-methyleneaminopencillanic acid.

The following may be mentioned from the cephalosporin group, for example, cafaclor, cefazaflur, cefazolin, cefadroxil, cefoxitin, cefuroxim, cephacetril, cephalexin, cephaloglycin, cephaloridines, cephalotin, cefamandol, cephanon, cephapirin, cefatrizin, cephradin, cefroxadin (7β-[D-2-amino-2-(1,4-cyclohexadienyl)acetamido]-3-methoxy-3-cephem-4-carboxylic acid=GCP 9000), cefsulodin, cefotaxim, cefotiam, ceftezol or cefazedon.

Of the nocardicines, for example nocardicine A may be mentioned, and of the thienamycins and clavulanic acids, for example thienamycin and clavulanic acid may be mentioned.

Of the aminoglycosides, there may be mentioned especially streptomycins, for example streptomycin and streptomycin A, neomycins, for example neomycin B, tobramycins, for example tobramycin or dibekacin, kanamycins (for example mixtures of kanamycin A, B and C), as well as amicacins, gentamycins (for example mixtures of gentamycin A, C$_1$, C$_2$ or C$_{1a}$), or sisomicins, such as sisomicin or netilmicin, and also lividomycin, ribocamycin and paromomycin.

As tetracyclines, especially tetracycline, doxycycline, chlorotetracycline, oxytetracycline and methacycline are to be mentioned.

As macrolides there are to be mentioned, for example, maridomycin, spiramycins, such as spiramycin I, II and III, erythromycins, for example erythromycin, oleandomycins, for example oleandomycin and tetraacetyloleandomycin, and as lincomycins, for example lincomycin and clindamycin.

As polyene antibiotics there are to be mentioned especially amphotericin B and its methyl esters or nystalin.

As polypeptide antibiotics, for example colistin, gramicidin S, polymyxin B, virginamycin, tyrothricin, viomycin or vancomycin may in particular be mentioned.

As rifamycins there come into consideration especially rifamycin S, rifamycin SV or rifamycin B or the semi-synthetic derivatives thereof, especially rifampicin.

The present application relates especially to compounds of the formula I in which X represents carbonyl, R$_1$ represents optionally substituted alkyl or aryl, R$_2$, R$_3$, R$_4$ and R$_6$ represent hydrogen or lower alkyl, R$_5$ represents hydrogen, lower alkyl optionally substituted by hydroxy, lower alkoxy, mercapto, lower alkylthio or halogen, or represents cycloalkyl or cycloalkyl-lower alkyl in each of which the cycloalkyl radical contains from 4 to 6 carbon atoms, optionally substituted phenyl or phenyl-lower alkyl, or heterocyclyl or heterocyclyl-lower alkyl each containing one or two nitrogen atoms, or R$_4$ and R$_5$ together alternatively represent alkylene having 3 or 4 carbon atoms, R$_7$ represents hydrogen and one of the radicals A$_1$ and A$_2$ represents a radical of the formula

(II)

in which T represents NH or O, in which Y is optionally substituted alkylene which may also be interrupted by oxycarbonyl or iminocarbonyl, and W represents an alkyl group having more than 6 carbon atoms optionally substituted by hydroxy, lower alkanoyloxy, amino, alkanoylamino or oxo, and the other of the radicals A$_1$ and A$_2$ represents hydroxy, lower alkoxy, amino or lower alkylamino, or represents aminocarbonyl-lower alkylamino optionally substituted in the lower alkyl radical by hydroxy, carboxy and/or amino, and the salts of these compounds.

The invention relates especially to compounds of the formula I in which X represents carbonyl, R$_1$ represents lower alkyl optionally substituted by hydroxy, lower alkoxy or halogen, or represents phenyl optionally substituted by hydroxy, lower alkoxy, lower alkyl or halogen, R$_2$, R$_4$ and R$_6$ represent hydrogen, R$_3$ represents hydrogen or lower alkyl, R$_5$ represents hydrogen, lower alkyl having from 1 to 3 carbon atoms optionally substituted by hydroxy, lower alkoxy, mercapto, lower alkylthio or halogen, or represents cycloalkyl or cycloalkyl-lower alkyl in which the lower alkyl radical contains from 1 to 3 carbon atoms, and in each of which the cycloalkyl radical contains from 4 to 6 carbon atoms, phenyl or phenyl-lower alkyl having from 1 to 3 carbon atoms in the lower alkyl radical, each optionally substituted by hydroxy, lower alkoxy or halogen, or heterocyclyl or heterocyclyl-lower alkyl having 1 to 3 carbon atoms in the lower alkyl radical and each containing one or two nitrogen atoms and having 5 or 6 ring members, or R$_4$ and R$_5$ together alternatively represent alkylene having 3 or 4 carbon atoms, R$_7$ represents hydrogen, and one of the radicals A$_1$ and A$_2$ represents a radical of the formula

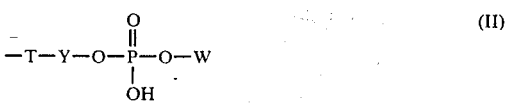

(II)

in which T represents NH or O, Y represents optionally substituted lower alkylene or a radical of the formula $$Y_1-COO-Y_2 \quad (IIIa)$$
$$Y_1-OOC-Y_2 \quad (IIIb)$$
$$Y_1-CO-\underset{\underset{R_8}{|}}{N}-Y_2 \quad (IIIc)$$

or $$Y_1-\underset{\underset{R_8}{|}}{N}CO-Y_2 \quad (IIId)$$

in which $Y_1$ and $Y_2$ each represents optionally substituted lower alkylene and $R_8$ represents hydrogen, W represents an alkyl group having from 10 to 25 carbon atoms and carrying in the 2-position a hydroxy group, an alkanoyloxy group, an amino group or an alkanoylamino group, and the other of the radicals $A_1$ and $A_2$ represents hydroxy, lower alkoxy, amino or lower alkylamino, or represents aminocarboxyl-lower alkylamino optionally substituted in the lower alkyl radical by hydroxy, carboxy or amino groups, and the salts of these compounds.

The invention relates especially to compounds of the formula I in which X represents carbonyl, $R_1$ represents lower alkyl having from 1 to 3 carbon atoms or phenyl, $R_2$, $R_4$ and $R_6$ represent hydrogen, $R_3$ represents hydrogen or lower alkyl having from 1 to 3 carbon atoms, $R_5$ represents hydrogen, lower alkyl having from 1 to 3 carbon atoms and optionally substituted by hydroxy, methoxy, mercapto, methylthio or halogen, or represents phenyl or phenylmethyl each optionally substituted by hydroxy, methoxy or halogen, or represents heterocyclyl or heterocyclylmethyl each containing one or two nitrogen atoms and having 5 ring members, or $R_4$ and $R_5$ together alternatively represent trimethylene, $R_7$ represents hydrogen, and one of the radicals $A_1$ and $A_2$ represents a radical of the formula $$-T-Y-O-\underset{\underset{OH}{|}}{\overset{\overset{O}{\|}}{P}}-O-W \quad (II)$$

in which
T represents NH or O,
Y represents lower alkylene having 2 or 3 carbon atoms or a radical of the formula (IIIa) or (IIIc)

$$Y_1-COO-Y_2 \quad (IIIa)$$
$$Y_1-CO-\underset{\underset{R_8}{|}}{N}-Y_2 \quad (IIIc)$$

in which
$R_8$ represents hydrogen and $Y_1$ and $Y_2$, independently of one another, each represents lower alkylene having from 1 to 3 carbon atoms optionally substituted by hydroxy, lower alkoxy, mercapto or lower alkylthio, or lower alkylene having from 1 to 3 carbon atoms substituted by optionally hydroxy-, methoxy- or halogen-substituted phenyl or phenyl-lower alkyl, or by heterocyclyl or heterocyclyl-lower alkyl having from 1 to 3 carbon atoms in the lower alkyl radical and each containing one or two nitrogen atoms and having 5 or 6 ring members,
W represents an alkyl group having from 10 to 25 carbon atoms substituted in the 2-position by hydroxy, lower alkanoyloxy, amino or alkanoylamino,
and the other of the radicals $A_1$ and $A_2$ represents hydroxy, lower alkoxy, amino, lower alkylamino or aminocarbonyl-lower alkylamino, and the salts of these compounds.

The invention relates especially to the novel muramyl peptides described in the Examples.

The novel compounds of the formula I can be obtained according to methods known per se.

Thus, they can be obtained by reacting a compound of the formula

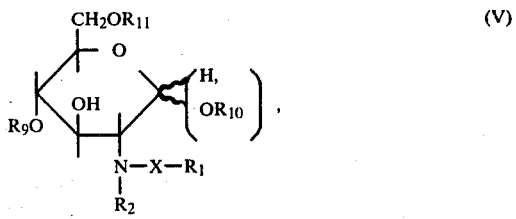

(V)

in which
X, $R_1$ and $R_2$ having the meanings given above and hydroxy groups optionally present therein are protected by a protecting group that can readily be split off, and
$R_9$, $R_{10}$ and $R_{11}$ represent a protecting group that can readily be split off, or a metal compound thereof, with a compound of the formula $$Z-\underset{\underset{R_3}{|}}{CH}-CON-\underset{\underset{R_4}{|}}{CH}-CON-\underset{\underset{R_6}{|}}{CH}-CH_2CH-COA_2 \quad (VI)$$

(with $R_5$, $COA_1$, $R_7$ substituents)

in which
Z represents a reactive esterified hydroxy group,
$R_3$, $R_4$, $R_5$, $R_6$, $R_7$, $A_1$ and $A_2$ have the meanings given above and hydroxy groups optionally present therein are protected by a protecting group that can readily be split off,
and protecting groups present are split off.

A reactive esterified hydroxy group is especially a hydroxy group esterified by a strong inorganic or organic acid, especially a hydroxy group that has been esterified by a hydrohalic acid, such as hydrochloric, hydrobromic or especially hydriodic acid.

A metal compound is especially a corresponding alkali metal derivative, for example a sodium or potassium derivative. It may be prepared, for example, by treating a compound of the formula V with a suitable base, such as a corresponding alkali metal compound, such as sodium hydride, sodium amide or butyllithium.

Protecting groups that can readily be split off are those known from peptide and sugar chemistry. For hydroxy groups the following should be given special mention: acyl radicals, for example lower alkanoyl radicals, such as acetyl, aroyl radicals, such as benzoyl, and especially radicals derived from carbonic acid derivatives, such as benzyloxycarbonyl or lower alkoxycarbonyl, or alkyl, especially tert.-butyl, benzyl optionally substituted by nitro, by lower alkoxy or by halogen, triphenylmethyl or tetrahydropyranyl each optionally substituted by halogen or by lower alkoxy such as methoxy, or optionally substituted alkylidene radicals that bond the oxygen atoms in the 4- and 6-position of the glucose moiety. Such alkylidene radicals are especially a lower alkylidene radical, especially the methylidene, isopropylidene or propylidene radical, or alternatively an optionally substituted benzylidene radical.

These protecting groups can be split off in a manner known per se. Thus, they can be removed by acid hydrolysis, and benzyl or benzylidene radicals can also be removed by hydrogenolysis, for example with hydrogen in the presence of a noble metal catalyst, such as a palladium or platinum catalyst.

The starting materials used are known or can be manufactured in a manner known per se.

The novel compounds can also be obtained by condensing in a manner known per se, a compound of the formula

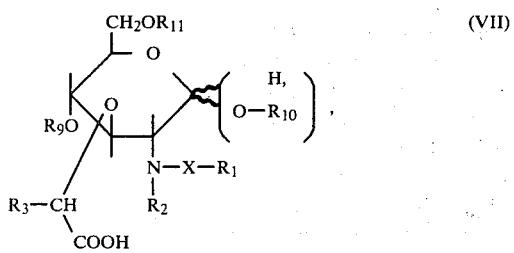 (VII)

in which

X, $R_1$, $R_2$ and $R_3$ have the meanings given above, and $R_9$, $R_{10}$ and $R_{11}$ represent hydrogen or a protecting group that can readily be split off, or a derivative thereof, with a compound of the formula

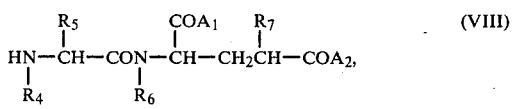 (VIII)

in which $R_4$, $R_5$, $R_6$, $R_7$, $A_1$ and $A_2$ have the meanings given above, provided that carboxy groups and, if desired, free hydroxy groups present in these radicals are protected by protecting groups that can readily be split off, or with a derivative thereof, and splitting off protecting group present.

The condensation is effected, for example, by reacting the acid (VII) in activated form with the amino compound (VIII), or reacting the acid (VII) with the compound (VIII), the amino group of which is present in the activated form. The activated carboxyl group may be, for example, an acid anhydride, preferably a mixed acid anhydride, for example with a carbonic acid lower alkyl ester, such as carbonic acid ethyl ester or isobutyl ester, an acid azide, an acid amide, such as an imidazolide, or an activated ester. Activated esters deserving special mention are: the cyanomethyl ester, carboxymethyl ester, p-nitrophenylthio ester, p-nitrophenyl ester, 2,4,5-trichlorophenyl ester, pentachlorophenyl ester, N-hydroxysuccinimide ester, N-hydroxyphthalimide ester, 8-hydroxyquinoline ester, N-hydroxy-1,2-dihydro-1-ethoxycarbonylquinoline ester, or N-hydroxypiperidine ester, or enol esters that are formed with N-ethyl-5-phenylisoxazolium 3'-sulphonate. Activated esters can also be obtained, if desired, with a carbodiimide with the addition of N-hydroxysuccinimide, or with a 1-hydroxybenztriazole or 3-hydroxy-4-oxo-3,4-dihydrobenz[d]-1,2,3-triazine, the two latter each being unsubstituted or substituted, for example by halogen, methyl or methoxy.

The amino group is activated for example by reaction with a phosphite.

Among the methods of the reaction with activated acids, especially those with N-ethyl-5-phenylisoxazolium 3'-sulphonate (Woodward reagent K) or 2-ethoxy-1,2-dihydro-1-ethoxycarbonylquinoline or carbodiimide should be mentioned.

Protecting groups that can readily be split off are those that are known from peptide and sugar chemistry. For carboxy groups, special mention should be given to tertiary butyl, benzyl or benzhydryl and, for hydroxy groups, to acyl radicals, for example lower alkanoyl radicals such as acetyl, aroyl radicals, such as benzoyl, and especially radicals derived from carbonic acid derivatives, such as benzyloxycarbonyl or lower alkoxycarbonyl, or alkyl, especially tert.-butyl, benzyl optionally substituted by nitro, by lower alkoxy or by halogen, triphenylmethyl or tetrahydropyranyl each optionally substituted by halogen or by lower alkoxy, such as methoxy, or optionally substituted alkylidene radicals that bond the oxygen atoms in the 4- and 6-position of the glucose moiety. Such alkylidene radicals are especially a lower alkylidene radical, especially the methylidene, isopropylidene or propylidene radical, or alternatively an optionally substituted benzylidene radical, preferably substituted in the p-position.

These protecting groups can be split off in a manner known per se. Thus, they can be removed by acid hydrolysis, and benzyl or benzylidene radicals can also be removed by hydrogenolysis, for example with hydrogen in the presence of a noble metal catalyst, such as a palladium or platinum catalyst.

The starting materials used are known or can be manufactured in a manner known per se.

Another process method of manufacturing these novel compounds consists in condensing a compound of the formula

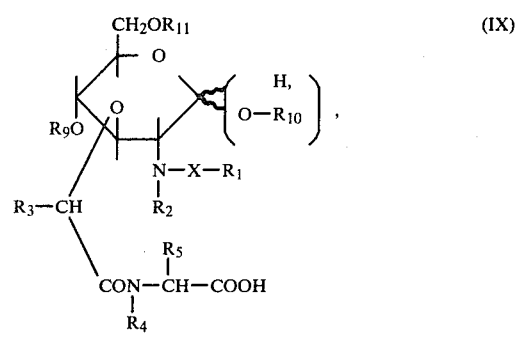 (IX)

in which

X, $R_1$, $R_2$, $R_3$, $R_4$ and $R_5$ have the meanings given above, provided that free hydroxy groups contained therein are optionally protected by a protecting group that can readily be split off, and $R_9$, $R_{10}$ and $R_{11}$ represent hydrogen or protecting groups that can readily be split off, or derivatives thereof, with a compound of the formula

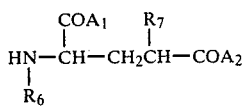

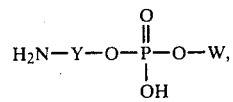

in which $R_6$, $R_7$, $A_1$ and $A_2$ have the meanings given above, provided that free carboxyl groups present in the radicals $R_7$, $A_1$ and $A_2$ are protected by protecting groups that can readily be split off, and splitting off protecting groups present.

The condensation is effected, for example by reacting the acid IX in activated form with the amino compound X, or reacting the acid IX with the compound X, the amino group of which is present in activated form. The activated carboxyl group can be, for example, an acid anhydride, preferably a mixed acid anhydride, an acid amide or an activated ester. Those which may be especially considered are the above-mentioned acid anhydrides, amides or esters. The amino group is activated for example by reaction with a phosphite.

The protecting groups that can readily be split off also correspond to those already mentioned above. They can be split off in a manner known per se by acid hydrolysis, or, in the case of benzyl or benzylidene radicals, also by hydrogenolysis, for example with hydrogen in the presence of a noble metal catalyst, such as a palladium or platinum catalyst.

The starting materials can be obtained in a manner known per se. Thus, for example, corresponding sugars unsubstituted in the 3-position can be reacted with a halo-$R_3$-acetic acid $R_4$-amide, or a compound of the formula VII can be reacted, in the manner indicated above, with an $R_4$-amino-$R_5$-acetic acid, the carboxyl group of which is protected, and the protecting groups can be split off.

Another process method for manufacturing these novel compounds of the formula I in which T represents NH, consists in condensing, in a manner known per se, a compound of the formula in which Y and W have the meanings given above, and splitting off optionally present protecting groups.

The activated carboxylic acid groups $COA_1°$ and $COA_2°$, respectively, may, for example, be an acid anhydride, for example with a carbonic acid lower alkyl ester, such as carbonic acid ethyl ester or isobutyl ester, an acid azide, an acid amide, such as an imidazolide or isoxazolide, or an activated ester. Activated esters deserving special mention are: the cyanomethyl ester, carboxymethyl ester, p-nitrophenylthio ester, methoxyethylthio ester, acetylaminoethylthio ester, p-nitrophenyl ester, 2,4,5-trichlorophenyl ester, N-hydroxysuccinimide ester, N-hydroxyphthalimide ester, 8-hydroxyquinoline ester and N-hydroxypiperidine ester. Active esters can also be obtained, if desired, with a carbodiimide with the addition of N-hydroxysuccinimide, or a 1-hydroxybenztriazole or 3-hydroxy-4-oxo-3,4-dihydrobenz[d]-1,2,3-triazine, the latter two each being unsubstituted or substituted, for example by halogen, methyl or methoxy.

Preferred active esters are those with N-hydroxysuccinimide or the C-substitution products thereof, such as N-hydroxymethylsuccinimide or N-hydroxydimethylsuccinimide, or the reaction with a carbodiimide, such as carbodiimide itself or 1-ethyl-3-(3-dimethylaminopropyl)carbodiimide.

The starting materials used for this purpose are known or can be manufactured in a manner known per se.

If, in the novel compounds of the formula I, T represents O, the compounds can also be obtained by esterifying, in a manner known per se, a compound of the formula

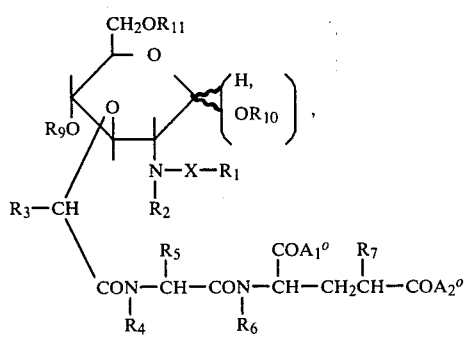

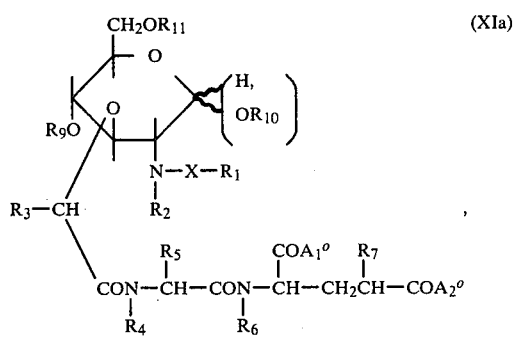

in which
X, $R_1$, $R_2$, $R_3$, $R_4$, $R_5$, $R_6$ and $R_7$ have the meanings given above,
$R_9$, $R_{10}$ and $R_{11}$ represent hydrogen or a protecting group that can readily be split off, and
one of the radicals $A_1°$ and $A_2°$ represents an activated hydroxy group and the other represents etherified hydroxy, amino, lower alkylamino or aminocarbonyl-lower alkylamino,
with a compound of the formula in which
X, $R_1$, $R_2$, $R_3$, $R_4$, $R_5$, $R_6$ and $R_7$ have the meanings given above,
$R_9$, $R_{10}$ and $R_{11}$ represent hydrogen or a protecting group that can readily be split off, and
one of the radicals $A_1°$ and $A_2°$ represents a hydroxy group and the other represents etherified hydroxy, amino, lower alkylamino or aminocarbonyl-lower alkylamino,
with a compound of the formula

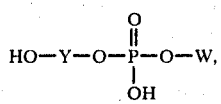
(XIIa)

in which Y and W have the meanings given above, wherein the acid XIa or the alcohol XIIa is present in reactive form, and splitting off optionally present protecting groups.

This reaction can be carried out by esterifying the free acid with the alcohol in the presence of an agent splitting off water, such as a carbodiimide, for example dicyclohexylcarbodiimide, and an amine, such as pyridine or dimethylaminopyridine, or a trialkylamine, for example trimethylamine. Alternatively, the carboxylic acid may be reacted, for example in the form of a salt, such as the sodium or potassium salt, with a reactive ester of the alcohol, for example an ester with a strong inorganic or organic acid, such as a hydrohalic acid, for example hydrochloric, hydrobromic or hydriodic acid, or with an organic sulphonic acid, such as p-toluenesulphonic acid or methanesulphonic or ethanesulphonic acid.

Furthermore, it is also possible to react the alcohol, optionally in the form of a salt, for example the sodium or potassium salt, with an activated carboxylic acid. Activated carboxylic acids deserving special mention are anhydrides, especially mixed acid anhydrides, acid azides, halides or activated esters, such as the cyanomethyl ester, carboxymethyl ester, p-nitrophenylthio ester, p-nitrophenyl ester, 2,4,5-trichlorophenyl ester, pentachlorophenyl ester, N-hydroxysuccinimide ester, N-hydroxyphthalimide ester, 8-hydroxyquinoline ester, 2-hydroxy-1,2-dihydro-1-ethoxycarbonylquinoline ester or N-hydroxypiperidine ester, or enol esters that are obtained with N-ethyl-5-phenylisoxazolium 3'-sulphonate. Activated esters can also be obtained, if desired, with a carbodiimide with the addition of N-hydroxysuccinimide, or a 1-hydroxybenztriazole or 3-hydroxy-4-oxo-3,4-dihydrobenz[d]-1,2,3-triazine, the latter two each being unsubstituted or substituted, for example by halogen, methyl or methoxy.

Protecting groups that can readily be split off are those known from peptide and sugar chemistry. For carboxy groups special mention should be given to tertiary butyl, benzyl or benzhydryl, and, for hydroxy groups, to acyl radicals, for example lower alkanoyl radicals such as acetyl, aroyl radicals, such as benzoyl, and especially to radicals that are derived from carbonic acid, such as benzyloxycarbonyl or lower alkoxycarbonyl, or alkyl, especially tert.-butyl, benzyl optionally substituted by nitro, by lower alkoxy or by halogen, triphenylmethyl or tetrahydropyranyl each optionally substituted by halogen or lower alkoxy, such as methoxy, or optionally substituted alkylidene radicals that bond the oxygen atoms in the 4- and 6-position of the glucose moiety. Such alkylidene radicals are especially a lower alkylidene radical, more especially the ethylidene, isopropylidene or propylidene radical, or alternatively an optionally substituted benzylidene radical, preferably substituted in the p-position.

These protecting groups can be split off in a manner known per se. Thus, they can be removed by acid hydrolysis, and benzyl or benzylidene radicals can also be removed by hydrogenolysis, for example with hydrogen in the presence of a noble metal catalyst, such as a palladium or platinum catalyst.

Furthermore, it is also possible to obtain the novel compounds of the formula I in which X represents a carbonyl group and $R_2$ represents hydrogen when, in a compound of the formula

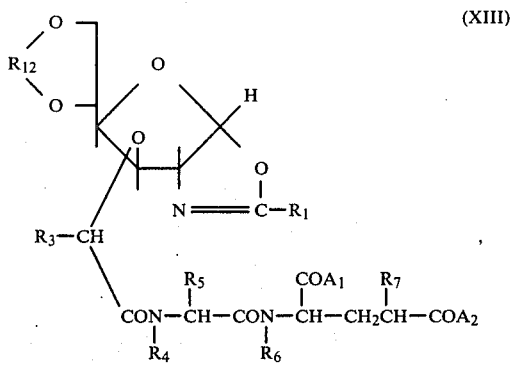
(XIII)

in which
$R_1$, $R_3$, $R_4$, $R_5$, $R_6$, $R_7$, $A_1$ and $A_2$ have the meanings given above, and
$R_{12}$ represents an alkylidene or cycloalkylidene group, the oxazoline and the dioxolane rings are split open by acid means and optionally present protecting groups are split off.

Alkylidene therein is especially lower alkylidene, such as isopropylidene, and cycloalkylidene, especially cyclopentylidene or cyclohexylidene.

This splitting is likewise carried out in a manner known per se, for example with an acidic ion exchanger, especially one with sulphonic acid groups such as Amberlite IR-120 (a styrene resin with strongly acidic sulpho groups) or Dowex 50 (polystyrenesulphonic acids) or with a strong inorganic or organic acid, such as hydrochloric acid, hydrobromic acid, sulphuric acid or a sulphonic acid, for example methanesulphonic acid, or with a phenylsulphonic acid optionally substituted in the aromatic ring, such as p-toluenesulphonic acid, or trifluoroacetic acid. If the operation is carried out in the presence of water, a free hydroxy group is obtained in the 1-position. If also one of the carboxyl groups $A_1$ or $A_2$ and/or $R_7$ is esterified by an alcohol, especially a lower alkanol, it can be saponified, especially at elevated temperature, with aqueous acid.

In the resulting compounds, protecting groups at the peptide radical can be split off subsequently, for example by hydrogenolysis, for example with catalytically activated hydrogen, or by hydrolysis.

The starting materials used therein can be obtained, for example, by introducing the $R_3$-acetylamino peptide radical in one or more stages into a corresponding oxazoline with a free hydroxy group in the 3-position of the sugar radical.

Compounds of the formula I in which Y represents a radical of the formula IIIc or IIId, can also be obtained by condensing a compound of the formula

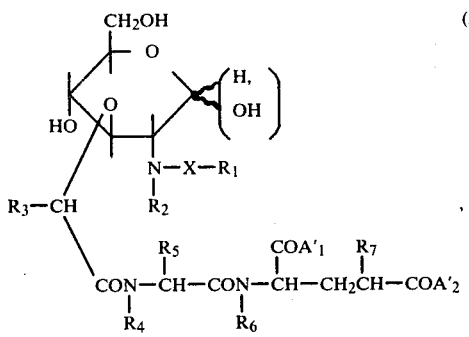

(XIV)

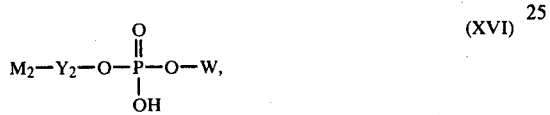

in which one of the radicals $A_1'$ and $A_2'$ represents a radical of the formula $$-T-Y_1-M_1 \qquad (XV)$$

and the other of the radicals $A_1'$ and $A_2'$ represents etherified hydroxy or amino, lower alkylamino or aminocarbonyl-lower alkylamino, with a compound of the formula $$M_2-Y_2-O-\underset{\underset{OH}{|}}{\overset{\overset{O}{\|}}{P}}-O-W, \qquad (XVI)$$

in which X, $R_1$, $R_2$, $R_3$, $R_4$, $R_5$, $R_6$, $R_7$, T, $Y_1$, $Y_2$ and W have the meanings given above and hydroxy groups present therein are optionally protected by protecting groups that can readily be split off, and one of the radicals $M_1$ and $M_2$ represents a free amino group or an activated derivative thereof, and the other represents a carboxylic acid group or an activated derivative thereof, and splitting off optionally present protecting groups.

Protecting groups that can readily be split off are those that are known from peptide and sugar chemistry. For carboxy groups, special mention should be given to tertiary-butyl, benzyl, triphenylmethyl or benzhydryl, the latter two each being optionally substituted by halogen or by lower alkoxy, such as methoxy, and, for hydroxy groups, to acyl radicals, for example lower alkanoyl radicals such as acetyl, aroyl radicals, such as benzoyl, and especially radicals derived from carbonic acid, such as benzyloxycarbonyl or lower alkoxycarbonyl, or alkyl, especially tert.-butyl, benzyl or tetrahydropyranyl, the latter two each being optionally substituted by nitro, by lower alkoxy or by halogen, or optionally substituted alkylidene radicals that bond the oxygen atoms in the 4- and 6-position of the glucose moiety. Such alkylidene radicals are especially a lower alkylidene radical, especially the ethylidene, isopropylidene or propylidene radical, or alternatively an optionally substituted benzylidene radical, preferably substituted in the p-position.

These protecting groups can be split off in a manner known per se. Thus, they can be removed by acid hydrolysis, and benzyl or benzylidene radicals can also be removed by hydrogenolysis, for example with hydrogen in the presence of a noble metal catalyst, such as a palladium or platinum catalyst.

The starting materials used are known or can be manufactured in a manner known per se.

The condensation is carried out, for example, by reacting the compound (XIV) in the form of the activated carboxylic acid with the amino compound (XVI), or reacting the acid (XIV) with the compound (XVI) of which the amino group is present in activated form. The activated carboxyl group may be, for example, an acid anhydride, preferably a mixed acid anhydride, such as, for example, with a carbonic acid lower alkyl ester, such as carbonic acid ethyl ester or isobutyl ester, an acid azide, an acid amide, such as an imidazolide or isoxazolide, or an activated ester. Activated esters are especially the cyanomethyl ester, carboxymethyl ester, p-nitrophenylthio ester, p-nitrophenyl ester, 2,4,5-trichlorophenyl ester, pentachlorophenyl ester, N-hydroxysuccinimide ester, N-hydroxyphthalimide ester, 8-hydroxyquinoline ester, 2-hydroxy-1,2-dihydro-1-ethoxycarbonylquinoline ester or N-hydroxypiperidine ester, or enol esters that have been obtained with N-ethyl-5-phenylisoxazolium 3'-sulphonate. Activated esters can also, if desired, be obtained with a carbodiimide with the addition of N-hydroxysuccinimide, or a 1-hydroxybenztriazole or 3-hydroxy-4-oxo-3,4-dihydrobenz[d]-1,2,3-triazine, the latter two each being unsubstituted or substituted, for example by halogen, methyl or methoxy.

The amino group is activated for example by reaction with a phosphite.

Among the methods of the reaction with activated acids, those with N-ethyl-5-phenylisoxazolium 3'-sulphonate (Woodward reagent K) or 2-ethoxy-1,2-dihydro-1-ethoxycarbonylquinoline or carbodiimide deserve special mention.

Compounds of the formula I in which Y represents a radical of the formula IIIa or IIIb may also be obtained by esterifying a compound of the formula

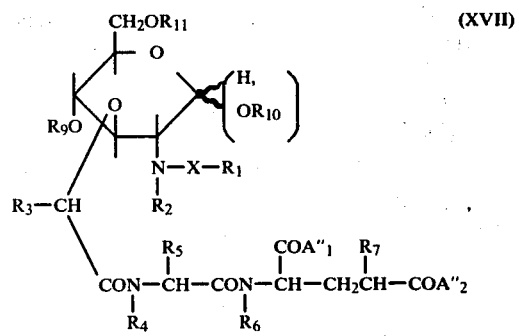

(XVII)

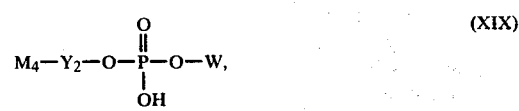

in which one of the radicals $A_1''$ and $A_2''$ represents a radical of the formula $$-T-Y_1-M_3 \qquad (XVIII)$$

in a manner known per se with a compound of the formula $$M_4-Y_2-O-\underset{\underset{OH}{|}}{\overset{\overset{O}{\|}}{P}}-O-W, \qquad (XIX)$$

in which
X, $R_1$, $R_2$, $R_3$, $R_4$, $R_5$, $R_6$, $R_7$, T, $Y_1$, $Y_2$ and W have the meanings given above, and hydroxy groups optionally present therein are protected by protecting groups that can readily be split off, $R_9$, $R_{10}$ and $R_{11}$ represent protecting groups that can readily be split off, and the other of the radicals $A_1''$ and $A_2''$ represents etherified hydroxy, amino, lower alkylamino or aminocarbonyl-lower alkylamino, and one of the radicals $M_3$ and $M_4$ represents a free hydroxy group and the other represents a free carboxyl group, one of the two radicals $M_3$ and $M_4$ optionally being present in reactive form, and splitting off optionally present protecting groups.

This reaction can be carried out by esterifying the free acid with an alcohol in the presence of an agent splitting off water, such as a carbodiimide, for example dicyclohexylcarbodiimide, and an amine, such as pyridine, dimethylaminopyridine, or a trialkylamine, for example trimethylamine. Alternatively, the carboxylic acid may be reacted, for example in the form of a salt, with a reactive ester of the alcohol, for example an ester with a strong inorganic or organic acid, such as a hydrohalic acid, for example hydrochloric, hydrobromic or hydriodic acid, or with an organic sulphonic acid, such as p-toluenesulphonic acid or methanesulphonic or ethanesulphonic acid.

Furthermore, it is also possible to react the alcohol, optionally in the form of a salt, for example the sodium or potassium salt, with an activated carboxylic acid. Activated carboxylic acids are especially anhydrides, especially mixed acid anhydrides, such as an acid azide or halide or an activated ester, such as the cyanomethyl ester, carboxymethyl ester, p-nitrophenylthio ester, p-nitrophenyl ester, 2,4,5-trichlorophenyl ester, pentachlorophenyl ester, N-hydroxysuccinimide ester, N-hydroxyphthalimide ester, 8-hydroxyquinoline ester, 2-hydroxy-1,2-dihydro-1-ethoxycarbonylquinoline ester or N-hydroxypiperidine ester, or enol esters that are obtained with N-ethyl-5-phenylisoxazolium 3'-sulphonate. Activated esters can also be obtained, if desired, with a 1-hydroxybenztriazole or 3-hydroxy-4-oxo-3,4-dihydrobenz[d]-1,2,3-triazine each unsubstituted or substituted, for example by halogen, methyl or methoxy.

Protecting groups that can readily be split off are those known from peptide and sugar chemistry. For carboxy groups special mention should be given to tertiary butyl, benzyl, or triphenylmethyl or benzhydryl, each of the latter two being optionally substituted by halogen or by lower alkoxy, such as methoxy, and, for hydroxy groups, to acyl radicals, for example lower alkanoyl radicals, such as acetyl, aroyl radicals such as benzoyl, and especially radicals derived from carbonic acid, such as benzyloxycarbonyl or lower alkoxycarbonyl, or alkyl, especially tert.-butyl, benzyl or tetrahydropyranyl, each of the latter two being optionally substituted by nitro, by lower alkoxy or by halogen, or optionally substituted alkylidene radicals that bond the oxygen atoms in the 4- and 6-position of the glucose moiety. Such alkylidene radicals are especially a lower alkylidene radical, especially the ethylidene, isopropylidene or propylidene radical, or alternatively an optionally substituted benzylidene radical, preferably substituted in the p-position.

These protecting groups can be split off in a manner known per se. Thus, they can be removed by acid hydrolysis, and benzyl or benzylidene radicals can also be removed by hydrogenolysis, for example with hydrogen in the presence of a noble metal catalyst, such as a palladium or platinum catalyst.

The starting materials used are known and can be manufactured in a manner known per se.

A further process method for the manufacture of the novel compounds of the formula I consists in reacting a compound of the formula

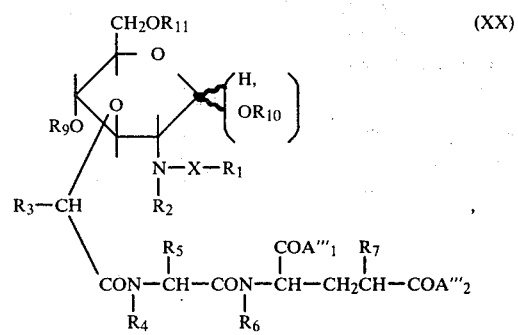

(XX)

in which

X, $R_1$, $R_2$, $R_3$, $R_4$, $R_5$, $R_6$ and $R_7$ have the meanings given above, and hydroxy groups optionally present therein are protected by a protecting group that can readily be split off, $R_9$, $R_{10}$ and $R_{11}$ represent protecting groups that can readily be split off, and one of the radicals $A_1'''$ and $A_2'''$ represents —T—Y—OH in which Y and T have the meanings given above, and the other of radicals $A_1'''$ and $A_2'''$ represents free or etherified hydroxy, amino or lower alkylamino, or represents aminocarbonyl-lower alkylamino optionally substituted in the lower alkyl radical, with a compound yielding the radical of the formula

(XXI)

in which

represents an electron pair, or oxo, if

represents an electron pair, oxidising with a weak oxidising agent, and splitting off protecting groups present.

As compounds yielding a radical of the formula XXI, compounds of the formula

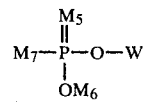

in which w and $\overset{M_5}{\underset{\|}{}}$ have the meanings given above,

M₆ represents hydrogen or a protecting group that can readily be split off, and

M₇ is a hydroxy group optionally present in reactive form, shall be given special mention. If M₆ is hydrogen, the compounds yielding the radical of the formula XXI are present predominantly in the tautomeric form, M₆ being linked directly to the phosphorus atom.

A protecting group M₆ that can readily be split off is especially lower alkyl, such as methyl or ethyl, lower alkenyl, such as ethenyl, allyl or 1-methylpropenyl, or benzyl.

A hydroxy group M₇ optionally present in reactive form is especially the free hydroxy group, or a hydroxy group esterified by a strong inorganic or organic acid, such as a hydroxy group esterified by a hydrohalic acid, a lower alkanecarboxylic acid or aryl- or alkylsulphonic acid, for example p-toluenesulphonic acid, methanesulphonic or ethanesulphonic acid. Alternatively, the radical M₇ may represent a phenoxy or lower alkoxy group.

This reaction is preferably carried out in the presence of an acid-binding agent, such as pyridine, a tri-lower alkylamine, for example triethylamine or trimethylamine, an imidazole, or an inorganic base, such as sodium or potassium hydroxide, or in the presence of a sodium or potassium alcoholate, an aprotic solvent, such as dimethyl sulphoxide or acetonitrile, being preferred as solvent.

If, in the resulting compounds, $\overset{M_5}{\underset{\|}{}}$ is an electron pair, oxidation is carried out, for example with a peracid, such as perbenzoic acid, or with an alkyl hydrogen oxide.

The splitting off of a protecting group M₆ usually takes place concurrently with splitting off of the remaining protecting groups. These can be removed in a manner known per se, for example by hydrogenolysis, for example with hydrogen in the presence of a noble metal catalyst, such as a palladium or platinum catalyst, or by acid hydrolysis.

The starting materials are known and can be manufactured in a manner known per se, for example by one of the above-mentioned suitably modified methods.

Furthermore, the novel compounds of the formula I can also be manufactured by reacting a compound of the formula

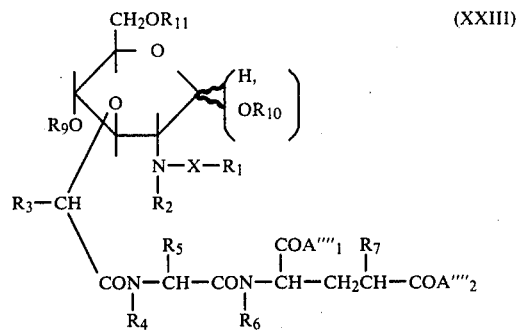

in which

X, R₁, R₂, R₃, R₄, R₅, R₆ and R₇ have the meanings given above, and hydroxy groups optionally present therein are protected by a protecting group that can readily be split off, R₉, R₁₀ and R₁₁ represent protecting groups that can readily be split off, and one of the radicals A₁'''' and A₂'''' represents

and the other represents free or etherified hydroxy, amino, lower alkylamino or aminocarbonyl-lower alkylamino, wherein T, Y, M₅, M₆ and M₇ have the meanings given above, with a compound of the formula

HO—W          (XXV), in which W has the meaning given above, if

represents an electron pair, oxidising with a weak oxidising agent, and splitting off protecting groups present.

A protecting group M₆ that can readily be split off is especially lower alkyl, such as methyl or ethyl, lower alkenyl, such as ethenyl, allyl or 1-methylpropenyl, or benzyl.

A hydroxy group M₇ optionally present in reactive form is especially the free hydroxy group or a hydroxy group esterified by a strong acid, such as a hydroxy group esterified by a hydrohalic acid, a nitroalkane-carboxylic acid or an arylsulphonic or alkylsulphonic acid, for example p-toluenesulphonic acid, methanesulphonic or ethanesulphonic acid. It may, however, alternatively represent a phenoxy or lower alkoxy group.

This reaction is preferably carried out in the presence of an acid-binding agent, such as pyridine, a tri-lower alkylamine, for example triethylamine or trimethylamine, an imidazole or an inorganic base, such as sodium or potassium hydroxide, or in the presence of a sodium or potassium alcoholate, an aprotic solvent, such as dimethyl sulphoxide or acetonitrile, being preferred as solvent.

If, in the resulting compounds, $$\overset{M_5}{\|}$$

is an electron pair, oxidation is carried out, for example, with a peracid, such as perbenzoic acid, or an alkyl hydrogen oxide.

The splitting off of a protecting group $M_6$ usually takes place concurrently with splitting off of the remaining protecting groups. These can be removed in a manner known per se, for example by hydrogenolysis, for example with hydrogen in the presence of a noble metal catalyst, such as a palladium or platinum catalyst, or by acid hydrolysis.

The starting materials are known and can be manufactured in a manner known per se, for example by one of the above-mentioned suitably modified methods.

The processes described above are carried out according to methods known per se in the absence or preferably in the presense of diluents or solvents, if necessary while cooling or heating, at elevated pressure and/or in an inert gas atmosphere, such as a nitrogen atmosphere.

Taking into consideration all the substituents present in the molecule, especially mild reaction conditions, such as short reaction times, the use of mild acidic or basic agents in low concentrations, stoichiometric quantitative ratios, the selection of suitable catalysts, solvents, temperature and/or pressure conditions, should, if necessary, be applied, especially when readily hydrolysable O-acyl radicals are present.

The invention relates also to those embodiments of the process in which a compound obtainable as an intermediate at any stage of the process is used as starting material and the remaining process steps are carried out, or the process is discontinued at any stage, or a starting material is formed under the reaction conditions or is used in the form of a reactive derivative or salt. The starting materials used are preferably those which, according to the process, result in the compounds described above as being especially valuable.

The present invention relates likewise to pharmaceutical preparations that contain compounds of the formula I. The pharmaceutical preparations according to the invention are those for enteral, such as oral, nasal or rectal, administration or for parenteral administration to warm-blooded animals, which contain the pharmacological active substance alone or together with a pharmaceutically acceptable carrier. The dosage of the active substance depends on the species of warmblooded animal, the age and the individual condition and also on the method of administration.

The novel pharmaceutical preparations contain from approximately 10% to approximately 95%, preferably from approximately 20% to approximately 90%, of the active substance. The pharmaceutical preparations according to the invention may, for example, be in the form of unit doses, such as dragees, tablets, capsules, suppositories or ampoules.

The pharmaceutical preparations of the present invention are prepared in a manner known per se, for example by means of conventional mixing, granulating, coating, dissolving or lyophilising processes. In addition to the types of administration mentioned, pharmaceutical preparations especially for oral administration can also be obtained by combining the active substance with solid carriers, if desired granulating a resulting mixture and processing the mixture or granulate, if desired or necessary after the addition of suitable adjuncts, to form tablets or dragee cores. They may also be incorporated in synthetic carriers which release the active substances in doses or allow them to diffuse.

Suitable carriers are especially fillers, such as sugars, for example lactose, saccharose, mannitol or sorbitol, cellulose preparations and/or calcium phosphates, for example tri-calcium phosphate or calcium hydrogen phosphate, also binders, such as starch pastes, using, for example, maize, wheat, rice or potato starch, gelatin, tragacanth, methylcellulose, hydroxypropylmethylcellulose, sodium carboxymethylcellulose and/or polyvinylpyrrolidone, and/or, if desired, disintegrating agents, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talcum, stearic acid or salts thereof, such as magnesium or calcium stearate, and/or polyethylene glycol. Dragee cores are provided with suitable coatings which may optionally be resistant to gastric juices, there being used, inter alia, concentrated sugar solutions, which optionally contain gum arabic, talcum, polyvinylpyrrolidone, polyethylene glycol and/or titanium dioxide, and lacquer solutions in suitable organic solvents or solvent mixtures, or, for the preparation of coatings resistant to gastric juices, solutions of suitable cellulose preparations, such as acetylcellulose phthalate or hydroxypropylmethylcellulose phthalate. Colouring substances or pigments may be added to the tables or dragee coatings, for example for identification or for indicating different doses of active substance.

The following Examples illustrate the above-described invention; they are not intended, however, to limit the scope thereof in any way. Temperatures are given in degrees Centigrade.

The compounds of the formula I according to the invention cannot be characterized by a melting point nor are spectroscopic data such as NMR and IR spectra suitable for satisfactory characterisation.

Furthermore, $R_f$ values are also unsuitable for precise characterisation because of the dominating nature of the lipid moieties.

Since, however, the structure of the starting materials is known exactly and since the linking thereof is clear, the sequence of the building blocks in the end product and the structure thereof is therefore also clear.

EXAMPLE 1

A solution of 2 mmoles of N-acetylmuramyl-L-alanyl-D-isoglutamine N-hydroxysuccinimide ester in 6.5 ml of dimethylacetamide is added dropwise to a solution of 1.4 mmole of 2-(hexadecyloxyhydroxyphosphoryloxy)ethylamine and of 3 mmoles of triethylamine in 25 ml of a mixture of chloroform/methanol/water, 65:25:4. After stirring for 18 hours at 20° C., the solutoon is concentrated at reduced pressure to approximately 15 ml; in the course of this an emulsion is formed. This is diluted with 100 ml of water and freeze-dried. The residue is suspended in 25 ml of water and extensively dialysed against water. The inner dialysate, which contains the desired product, is freeze-dried. N-Acetylmuramyl-L-alanyl-D-isoglutamine 2-(hexadecyloxyhydroxyphosphoryloxy)ethylamide is purified by chromatography over a Sephadex LH-20 column. Eluant mixture: chloroform/methanol/acetic acid/water, 25:15:4:2.

The novel compound is characterised analytically by quantitative determination of the building blocks N-acetylmuramic acid, hexadecanol, phosphate, L-alanine and D-isoglutamic acid:

N-acetylmuramic acid is determined by spectrophotometry by means of the Morgan-Elson reaction according to the modification by J. M. Ghuyson et al. [in "Methods in Enzymology" 8, 629 (1966)].

Phosphate is quantitatively determined according to Lowry et al. [J. Biol. Chem. 207, 1 (1954)].

The amino acids and hexadecanol are quantitatively determined in a total hydrolysate (6 N HCl, 24 hours 110° C.) by means of an amino acid analyser, or by gas chromatography using norleucine or pentadecanol as internal standards.

The N-acetylmuramyl-L-alanyl-D-isoglutamine N-hydroxysuccinimide ester used as starting material may be produced, for example, as follows:

2 mmoles of N-acetylmuramyl-L-alanyl-D-isoglutamine, 2.2 mmoles of N-hydroxysuccinimide and 2.2 mmoles of dicyclohexylcarbodiimide are dissolved in 6.5 ml of dimethylacetamide and the solution is stirred for 18 hours at 20° C. The precipitated dicyclohexylurea is separated off and the solution is used directly for the condensation with the phospholipid.

2-(hexadecyloxyhydroxyphosphoryloxy)ethylamine used as starting material is a commercially available synthetic preparation.

EXAMPLE 2

In an analogous manner to Example 1, using 2-(hexadecyloxyhydroxyphosphoryloxy)ethylamine or 2-(cholest-5-ene-3β-oxyhydroxyphosphoryloxy)ethylamine or 2-(tetradecyloxyhydroxyphosphoryloxy)ethylamine, and the N-hydroxysuccinimide esters of corresponding muramyl peptides, the following are obtained:

N-acetyldesmethylmuramyl-L-alanyl-D-isoglutamine-2-hexadecyloxyhydroxyphosphoryloxy)ethylamide, N-acetyldesmethylmuramyl-L-alanyl-D-isoglutaminyl-L-alanine 2-(hexadecyloxyhydroxyphosphoryloxy)ethylamide, N-acetylmuramyl-L-alanyl-D-isoglutaminyl-L-alanine 2-(hexadecyloxyhydroxyphosphoryloxy)ethylamide, N-acetylmuramyl-L-alanyl-D-isoglutaminyloxymethylcarboxylic acid 2-(hexadecyloxyhydroxyphosphoryloxy)ethylamide, N-acetylmuramyl-L-alanyl-D-isoglutaminyl-L-alanyl-2-(tetradecyloxyhydroxyphosphoryloxy)ethylamide, N-acetyldesmethylmuramyl-L-alanyl-D-isoglutaminyl-2-(cholest-5-ene-3β-oxyhydroxyphosphoryloxy)ethylamide.

EXAMPLE 3

In an analogous manner to Example 1, using 2-[(3'R)-hydroxy-(2'S)-palmitoylamino-4't-octadecenyloxyhydroxyphosphoryloxy]ethylene (2-[N-palmitoylsphingosine-1-O-ylhydroxyphosphoryloxy]ethylamine) and N-acetylmuramyl-L-alanyl-D-isoglutamine N-hydroxysuccinimide ester, N-acetylmuramyl-L-alanyl-D-isoglutamine 2-[(3'R)-hydroxy-(2'S)-palmitoylamino-4't-octadecenyloxyhydroxyphosphoryloxy]ethylamide is obtained.

EXAMPLE 4

In an analogous manner to Example 1, using 2-[(3'R)-hydroxy-(2'S)-palmitoylamino-4't-octadecenyloxyhydroxyphosphoryloxy]ethylamine and corresponding muramyl peptide-N-hydroxysuccinimide esters, the following are obtained: N-acetyldesmethylmuramyl-L-alanyl-D-isoglutamine 2-[(3'R)-hydroxy-(2'S)-palmitoylamino-4't-octadecenyloxyhydroxyphosphoryloxy]ethylamide, N-acetyldesmethylmuramyl-L-alanyl-D-isoglutaminyl-L-alanine 2-[(3'R)-hydroxy-(2'S)-palmitoylamino-4't-octadecenyloxyhydroxyphosphoryloxy]ethylamide, N-acetylmuramyl-L-alanyl-D-isoglutaminyl-L-alanine-2-[(3'R)-hydroxy-(2'S)-palmitoylamino-4't-octadecenyloxyhydroxyphosphoryloxy]ethylamide, N-acetylmuramyl-L-alanyl-D-isoglutaminyloxymethylcarboxylic acid 2-[(3'R)-hydroxy-(2'S)-palmitoylamino-4't-octadecenyloxyhydroxyphosphoryloxy]ethylamide.

EXAMPLE 5

(a) 1 mmole (350 mg) of 1α-benzyl-2-acetamido-2-desoxy-4,6-isopropylidene glucose is left in 10 ml of absolute dimethoxyethane to react with 1 mmole of sodium hydride/mineral oil dipsersion until the evolution of $H_2$ is complete. The mixture is then cooled to 0° and, while stirring well and with the exclusion of moisture, 1 mmole of chloroacetyl-L-alanyl-D-isoglutamine 2-(hexadecyloxyhydroxyphosphoryloxy)ethylamide in the form of a pyridine salt in 5 ml of dimethoxyethane is added, and the reaction mixture is allowed to warm up to room temperature. After 3 hours at room temperature, the mixture is evaporated to dryness in vacuo and chromatographed over Merck silica gel in chloroform: methanol 7:3. The fractions that contain the desired end product react on the thin layer plate (silica gel, Merck) positively with phosphate reagent according to V. E. Vaskovsky and E. Y. Kostetsky, J. Lipid. Res. 9, 396 (1968) and positively with 2 N sulphuric acid at an elevated temperature (brown colouration of the sugar). They are concentrated by evaporation and, to remove the protecting groups, are first of all maintained at a temperature of 50° for 1 hour in a mixture of 12 ml of glacial acetic acid and 8 ml of water, and then hydrogenated at room temperature and normal pressure with 10% Pd/C. After 20 hours the α-benzyl group has been removed; the catalyst is filtered off and the filtrate is concentrated to a syrup by evaporation in vacuo. This yields the syrupy pyridinium salt of N-acetylnormuramyl-L-alanyl-D-isoglutamine 2-(hexadecyloxyhydroxyphosphoryloxy)ethylamide, which is converted into the semi-sodium salt by dialysis against 10% NaCl solution and then against distilled water. The substance is characterised by amino acid analysis, the determination of the ratio of P to Na and the determination of muramic acid according to Morgan-Elson as described in Example 1. $R_f$=0.25; eluant: $CHCl_3$:methanol:water=65:25:4 (v/v) on thin layer Merck silica gel plates.

(b) The α-benzyl-2-acetamido-2-desoxy-4,6-isopropylidene glucose used as starting material has the following physical properties: melting point 136°–137°, $[\alpha]_D^{20}$=+110° ($CHCl_3$, c=1), $R_f$=0.55 ($CH_2Cl_2$:methanol=5:1 on thin layer Merck silica gel plates).

The pyridinium salt of chloroacetyl-L-alanyl-D-isoglutamine 2-(hexadecyloxyhydroxyphosphoryloxy)ethylamide is obtained by reacting 2 mmoles of chloroacetyl-L-alanyl-D-isoglutamine 2-hydroxyethylamide in pyridine with 1.5 mmole of phosphoric acid hexadecyl ester and 4.5 mmoles of triisopropylbenzenesulphonic acid chloride at room temperature. After 15 hours, 2 ml of water are added, the mixture is left to stand at room temperature for 1 hour and evaporated to dryness in vacuo and the residue is dialysed against distilled water. The desired phosphoric acid diester remains in the dialysis tube. The contents of the tube are concentrated to a syrup by evaporation, and evaporation is then carried out in vacuo 4 times with pyridine for the azeotropic removal of water. Before further reaction, residual water can be removed in dimethoxyethane by a molecular sieve. $R_f=0.35$ ($CHCl_3$:methanol:$H_2O=65:25:4$, thin layer Merck silica gel plates).

EXAMPLE 6

(a) 1.2 mmole of dicyclohexylcarbodiimide and 1.3 mmole of N-hydroxysuccinimide are added to 410 mg (1 mmole) of 1α-benzyl-N-acetyl-4,6-isopropylidenenormuramic acid, 0.9 mmole of L-alanyl-D-isoglutamine 2-(hexadecyloxyhydroxyphosphoryloxy)ethylamide in a mixture of 15 ml of dimethylformamide, 10 ml of tetrahydrofuran and 2 ml of pyridine. After 24 hours at room temperature the reaction is complete. A few drops of water are added, the dicyclohexylurea formed is suction-filtered off and the filtrate is evaporated to dryness in vacuo. The residue is purified by chromatography over Merck silica gel in chloroform/methanol=7:3 (see Example 5). The fractions containing the end product are worked up analogously to Example 5, freed of protecting groups and then dialysed as described. In this manner the semi-sodium salt of N-acetylnormuramyl-L-alanyl-D-isoglutamine 2-(hexadecyloxyhydroxyphosphoryloxy)ethylamide, which in 1% aqueous solution has a pH value of 6.5, is obtained.

(b) The L-alanyl-D-isoglutamine 2-(hexadecyloxyhydroxyphosphoryloxy)ethylamide used as starting material is obtained analogously to Example 5b by condensing tertiary-butoxycarbonyl-L-alanyl-D-isoglutamine 2-hydroxyethylamide with phosphoric acid hexadecyl ester in pyridine by reacting with 3 equivalents of triisopropylbenzenesulphonic acid chloride, and subsequently splitting off the tertiary-butoxycarbonyl group with 20% trifluoroacetic acid in methylene chloride at room temperature. Evaporation to dryness in vacuo is then carried out and the residue is dialysed against phosphate buffer (pH=7), then against distilled water. The ethylamide remains in the dialysis tube and is obtained by freeze-drying the inner dialysate. Extraction of the lyophilisate with ethyl acetate removes residues of salts of triisopropylbenzenesulphonic acid.

1α-benzyl-4,6-isopropylidene-N-acetyldesmethylmuramic acid is obtained, in a form suitable for the coupling, from the corresponding methyl ester: melting point 122°-125°, $[\alpha]_D^{20}=+150°$ ($CHCl_3$, c=1), $R_f=0.53$ ($CH_2Cl_2$:methanol=15:1, thin layer Merck silica gel plates), by saponifying with KOH/methanol at room temperature and then adjusting the pH value to 6 with 1 N hydrochloric acid with a pH meter.

EXAMPLE 7

(a) Analogously to Example 6, 1 mmole of 1α-benzyl-N-acetyl-4,6-isopropylidenenormuramyl-L-alanine is condensed with 1 mmole of D-isoglutamine 2-(hexadecyloxyhydroxyphosphoryloxy)ethylamide in DMF/tetrahydrofuran with dicyclohexylcarbodiimide and hydroxysuccinimide. After working up analogously and splitting off the protecting groups, the pyridinium salt of N-acetylnormuramyl-L-alanyl-D-isoglutamide 2-(hexadecyloxyhydroxyphosphoryloxy)ethylamide is obtained which, according to analysis and $R_f$ value, is identical to the substance obtained according to Examples 5 and 6. The pyridinium salt can readily be converted into the semi-sodium salt by dialysis against sodium chloride solution at a pH of 7.

(b) The D-isoglutamine 2-(hexadecyloxyhydroxyphosphoryloxy)ethylamide used as starting material is obtained analogously to Example 5b by condensing phosphoric acid hexadecyl ester with tert.-butoxycarbonyl-D-isoglutamine 2-hydroxyethylamide in pyridine with 3 equivalents of triisopropylbenzenesulphonic acid chloride and subsequently splitting off the BOC group with 20% trifluoroacetic acid in methylene chloride at room temperature (4 hours). Dialysis against water yields the pure hydroxyphosphoryloxyethylamine in the form of an inner salt.

1α-benzyl-N-acetyl-4,6-isopropylidenenormuramyl-L-alanine is obtained by catalytic hydrogenation, with 5% Pd/C in tetrahydrofuran over a period of 30 minutes, of 1α-benzyl-N-acetyl-4,6-isopropylidenenormuramyl-L-alanine benzyl ester with the following constants: $[\alpha]_D^{20}=+73°$ ($CHCl_3$, c=1), $R_f=0.25$ (ethyl acetate, thin layer Merck silica gel plates).

EXAMPLE 8

(a) 1 mmole of 1α-benzyl-N-acetyl-4,6-isopropylidenenormuramyl-L-alanyl-D-isoglutamine is esterified with 0.8 mmole of 2-(hexadecyloxyhydroxyphosphoryloxy)ethanol in pyridine with 1.2 mmole of dicyclohexylcarbodiimide, 1.2 mmole of N-hydroxysuccinimide and 0.1 mmole of 4-dimethylaminopyridine (method according to Steglich, see B. Neises and W. Steglich, Angew. Chem. 90, 556 (1978)) at room temperature. After 24 hours at room temperature, a few drops of water are added and the dicyclohexylurea formed is suction-filtered off. The filtrate is evaporated to dryness in vacuo, taken up in 20 ml of 80% acetic acid and the isopropylidene groups are split off in the course of 1 hour at 50°. The solution is then hydrogenated analogously to Example 5 and the solution, freed of catalyst and diluted with 50 ml of water, is dialysed against buffered NaCl solution at a pH of 7, then against distilled water. In this manner the semi-sodium salt of N-acetylnormuramyl-L-alanyl-D-isoglutamine 2-(hexadecyloxyhydroxyphosphoryloxy)ethyl ester, $R_f=0.25$ ($CHCl_3$/methanol/$H_2O=65:25:4$, thin layer Merck silica gel plates, is obtained.

(b) The 2-(hexadecyloxyhydroxyphosphoryloxy)ethanol used as starting material is obtained according to methods known per se from phosphorus oxychloride and hexadecanol in tetrahydrofuran, with subsequent reaction with ethylene glycol and triethylamine and basic hydrolysis of the resulting product in tetrahydrofuran/water/sodium hydroxide solution at room temperature: cf H. Eibl and A. Nicksch, German Offenlegungsschrift No. 2 345 059 and P. Chabrier et al., C. R. Acad. Sci., Paris, Serie C 283, 229 (1976).

EXAMPLE 9

(a) 1 mmole of the pyridine salt of 1,2-[2-phenyl-$\Delta^2$-oxazoline(4,5)]-5,6-isopropylidene-D-glucofuranosyl-3-O-methylcarbonyl-L-alanyl-D-isoglutamine 2-(hexadecyloxyhydroxyphosphoryloxy)ethylamide is left to stand for 20 hours, at room temperature, in a mixture of 10 ml of methylene chloride and 10 ml of trifluoroacetic acid. After evaporating to dryness in vacuo, dialysing the residue against buffered NaCl solution of a pH of 7, then against distilled water, and freeze-drying the tube contents, N-benzoylnormuramyl-L-alanyl-D-isoglutamine 2-(hexadecyloxyhydroxyphosphoryloxy)ethylamide is obtained in the form of the semi-sodium salt having an $R_f$ value of 0.27 (CHCl$_3$:methanol:-H$_2$O=65:25:4, thin layer Merck silica gel plates).

(b) The starting material is obtained as follows:

Analogously to Example 6, 1 mmole of 2-phenyl-4,5-[3-carboxymethyl-5,6-isopropylidene-D-glucofurano]-$\Delta^2$-oxazoline is condensed with 0.8 mmole of L-alanyl-D-isoglutamine 2-(hexadecyloxyhydroxyphosphoryloxy)ethylamide with the aid of 1.2 mmole of dicyclohexylcarbodiimide and 1.3 mmole of N-hydroxysuccinimide in a mixture of 10 ml of dimethylformamide and 10 ml of tetrahydrofuran. After stirring for 24 hours at room temperature, a few drops of water are added, the precipitated dicyclohexylurea is suction-filtered off and the filtrate is evaporated to dryness in vacuo. By chromatography over Merck silica gel in chloroform/methanol 7:3, syrupy 1,2-[2-phenyl-$\Delta^2$-oxazoline(4,5)]-5,6-isopropylidene-D-glucofuranosyl-3-O-methylcarbonyl-L-alanyl-D-isoglutamine 2-(hexadecyloxyhydroxyphosphoryloxy)ethylamide is obtained in the form of an internal salt having an $R_f$ value of 0.40 (CHCl$_3$:methanol:H$_2$O=65:25:4, thin layer Merck silica gel plates).

EXAMPLE 10

(a) Analogously to Example 8, 1 mmole of 1α-benzyl-N-acetyl-4,6-isopropylidenedesmethylmuramyl-L-alanyl-D-isoglutamine 2-hydroxyethylamide is esterified with 0.8 mmole of hexadecyloxyhydroxyphosphoryloxyacetic acid according to the method of Steglich et al. [B. Neises and W. Steglich, Angew. Chem. 90, 556 (1978)]. After 20 hours at room temperature, a few drops of water are added, the dicyclohexylurea formed is suction-filtered off and the filtrate is evaporated to dryness in vacuo. By chromatography over Merck silica gel in chloroform/methanol 7:3, the muramyl peptide/phospholipid conjugate is obtained, which analogously to Example 5 is freed of protecting groups and purified by dialysis. N-acetylnormuramyl-L-alanyl-D-isoglutamine 2-(hexadecyloxyhydroxyphosphoryloxymethylcarbonyloxy)ethylamide is obtained in the form of a semi-sodium salt, $R_f$=0.27 (CHCl$_3$/methanol/H$_2$O=65:25:4, thin layer Merck silica gel plates).

(b) The 1α-benzyl-N-acetyl-4,6-isopropylidenenormuramyl-L-alanyl-D-isoglutamine 2-hydroxyethylamide used as starting material is obtained analogously to Example 6 by condensing 1α-benzyl-N-acetyl-4,6-isopropylidenenormuramyl-L-alanyl-D-isoglutamine with 2-aminoethanol, in the form of a colourless amorphous substance; $[\alpha]_D^{20}$= +85° (CHCl$_3$, c=1), $R_f$=0.38 (CHCl$_3$/methanol/H$_2$O=70:30:5, thin layer Merck silica gel plates).

The educt, 1α-benzyl-N-acetyl-4,6-isopropylidenenormuramyl-L-alanyl-D-isoglutamine, shows an $R_f$ value of 0.34 in this eluant. The corresponding $R_f$ values in the system ethyl acetate/n-butanol/pyridine/acetic acid/water 42:21:21:0.6:10 is for the educt 0.50 and for the hydroxyethylamide 0.64.

EXAMPLE 11

(a) The 1α-benzyl-N-acetyl-4,6-isopropylidenenormuramyl-L-alanyl-D-isoglutamine 2-hydroxyethylamide described in Example 10b is condensed with phosphoric acid hexadecyl ester in pyridine according to the method described in Example 5b. The pyridine salt of the corresponding phosphoric acid diester is obtained which, analogously to Example 5, is purified, freed of protecting groups and dialysed. After freeze-drying the inner dialysate, the end product N-acetylnormuramyl-L-alanyl-D-isoglutamine 2-(hexadecyloxyhydroxyphosphoryloxy)ethylamide is obtained, which contains 0.5 equivalents of Na$^+$ ions.

(b) 1 mmole of pyridinium salt of 1α-benzyl-N-acetyl-4,6-isopropylidenenormuramyl-L-alanyl-D-isoglutamine 2-[dihydroxyphosphoryloxyethyl]amide is condensed according to the method described in Example 5b with 2 mmoles of hexadecanol in pyridine. After working up analogously to Example 5a, splitting off the protecting groups, dialysing and freeze-drying the inner dialysate the end product is obtained.

EXAMPLE 12

The following compounds are obtained analogously to the manner described in Example 1:

N-acetylmuramyl-L-valyl-D-isoglutamine 2-(tetradecyloxyhydroxyphosphoryloxy)ethylamide, N-acetylmuramyl-L-valyl-D-isoglutaminyl-L-alanine 2-(cholest-5-ene-3β-oxyhydroxyphosphoryloxy)ethylamide, N-propionyldesmethylmuramyl-L-alanyl-D-isoglutamine 2-[(3'R)-hydroxy-(2'S)-palmitoylamino-4't-octadecenyloxyhydroxyphosphoryloxy]ethylamide, N-propionyldesmethylmuramyl-L-alanyl-D-isoglutaminyl-L-alanine 2-(tetradecyloxyhydroxyphosphoryloxy)ethylamide, N-acetylmuramyl-L-prolyl-D-isoglutamine 2-(cholest-5-ene-3β-oxyhydroxyphosphoryloxy)ethylamide, N-acetylmuramyl-L-prolyl-D-isoglutaminyl-L-alanine 2-(tetradecyloxyhydroxyphosphoryloxy)ethylamide, N-benzoyldesmethylmuramyl-L-α-aminobutyryl-D-isoglutamine 2-[(3'R)-hydroxy-(2'S)-palmitoylamino-4't-octadecenyloxyhydroxyphosphoryloxy]ethylamide, N-benzoyldesmethylmuramyl-L-seryl-D-isoglutamine 2-(hexadecyloxyhydroxyphosphoryloxy)ethylamide, N-acetyldesmethylmuramyl-L-seryl-D-glutaminyl-L-alanine 2-(cholest-5-ene-3β-oxyhydroxyphosphoryloxy)ethylamide, N-benzoylmuramyl-L-cysteinyl-D-glutamine 2-(tetradecyloxyhydroxyphosphoryloxy)ethylamide, N-acetylmuramyl-L-lysyl-D-glutamine 2-(hexadecyloxyhydroxyphosphoryloxy)ethylamide, N-propionyldesmethylmuramyl-N-methylalanylisoglutamine 2-(cholest-5-ene-3β-oxyhydroxyphosphoryloxy)ethylamide, N-acetylmuramyl-L-alanyl-N-methyl-D-isoglutamine 2-(hexadecyloxyhydroxyphosphoryloxy)ethylamide, N-acetyldesmethylmuramyl-L-arginyl-D-isoglutamine 2-(tetradecyloxyhydroxyphosphoryloxy)ethylamide, N-acetyldesmethylmuramyl-L-histidyl-D-isoglutamine 2-(hexadecyloxyhydroxyphosphoryloxy)ethylamide, N-butyryldesmethylmuramyl-L-phenylalanyl-D-isoglutamine 2-[(3'R)-hydroxy-(2'S)-palmitoylamino-4't-octadecenyloxyhydroxyphosphoryloxy]ethylamide, N-butyryldesmethylmuramyl-L-methionyl-D-glutamine 2-(cholest-5-ene-3β-oxyhydroxyphosphoryloxy)ethylamide, N-(n-pentanoyl)muramyl-L-tyrosyl-D-isoglutamine 2-(hexadecyloxyhydroxyphosphoryloxy)ethylamide, N-acetyl-N-methyldesmethylmuramyl-L-alanyl-D-glutamyl-α-glycinamide γ-[2-(hexadecyloxyhydroxyphosphoryloxy)ethyl]-amide, N-(4-methylbenzoyl)muramylglycyl-D-glutamyl-α-glycinamide γ-L-alanine 2-(tetradecyloxyhydroxyphosphoryloxy)ethylamide, N-ethoxycarbonylmuramyl-O-methyl-L-threonyl-D-isoglutamine 2-(hexadecyloxyhydroxyphosphoryloxy)ethylamide, N-(2-methoxyethylcarbonyl)desmethylmuramylphenylglycyl(γ-N-methylcarbamoyl-γ-aminobutyric acid 2-(tetradecyloxyhydroxyphosphoryloxy)ethylamide, N-(4-methoxybenzoyl)desmethylmuramyl(α-methoxycarbonyl-D-isoglutaminyl)glycyl-L-alanyl-2-(2-chloroheptyloxyhydroxy-phosphoryloxy)ethylamide, N-(4-chlorobenzoyl)desmethylmuramylsarcosyl-D-isoglutaminyloxymethylcarbonyloxymethylcarboxylic acid 2-(hexadecyloxyhydroxyphosphoryloxy)ethylamide.

EXAMPLE 13

A solution of 2 mmoles of N-acetylmuramyl-L-alanyl-D-isoglutamine N-hydroxysuccinimide ester in 6.5 ml of dimethylacetamide is added dropwise to a solution of 1.4 mmole of 2-(hexadecyloxyhydroxyphosphoryloxy)ethylamide and 3 mmoles of triethylamine in 25 ml of a mixture of chloroform, methanol and water, 65:25:4. After stirring for 18 hours at 20° C., the solution is concentrated to approximately 15 ml at reduced pressure; an emulsion is thus formed. This is diluted with 100 ml of water and freeze-dried. The residue is suspended in 25 ml of water and dialysed at 4° C. in the following sequence: 18 hours against water, 24 hours against 0.1 M sodium phosphate buffer-0.1 M NaCl solution of a pH of 7, and 48 hours against water. After the last dialysis the inner dialysate must be chloride-free. The inner dialysate, which contains the desired product, is centrifuged at 10,000 g and 20° C. for 30 minutes and the supernatant is freeze-dried. The isolated product is chromatographically pure N-acetyl-muramyl-L-alanyl-D-isoglutamine 2-(hexadecyloxyhydroxyphosphoryloxy)ethylamide, 0.54 mole equivalents of which are present in the form of Na+ salt. In thin layer chromatography over silica gel the compound has the following $R_f$ values: 0.24 (in chloroform/methanol/water, 65:25:4) and 0.58 (in chloroform/methanol/acetic acid-water, 25:15:4:2).

The new compound is analytically characterised by quantitative determination of the building blocks N-acetylmuramic acid, hexadecanol, phosphate, Na+, L-alanine and D-glutamic acid:

N-acetylmuramic acid is determined by spectrophotometry by means of the Morgan-Elson reaction according to the modification by J. M. Ghuyson et al. [in "Methods in Enzymology" 8, 629 (1966)].

Phosphate is quantitatively determined according to Lowry et al. [J. Biol. Chem. 207, 1 (1954)].

The amino acids and hexadecanol are quantitatively determined in a total hydrolysate (6 N HCl, 24 hours 110° C.) by means of an amino acid analyser or by gas chromatography using norleucine or pentadecanol as internal standards.

The molar ratios found, calculated on phosphate, are as follows:

$PO_4'''$: N-acetylmuramic acid: l-alanine: D-glutamic acid: hexadecanol: Na+32 1:0.93:0.94:0.91:1.1:0.94.

EXAMPLE 14

N-acetylmuramyl-L-alanyl-D-isoglutamine 2-[(3′R)-hydroxy-(2′S)-palmitoylaminooctadecyloxyhydroxyphosphoryloxy]ethylamide, N-acetylmuramyl-L-alanyl-D-isoglutaminyl-L-alanine 2-[(3′R)-hydroxy-(2′S)-palmitoylaminooctadecyloxyhydroxyphosphoryloxy]ethylamide and N-acetylmuramyl-L-α-aminobutyryl-D-isoglutaminyl-L-alanine 2-[(3′R)-hydroxy-(2′S)-palmitoylaminooctadecyloxyhydroxyphosphoryloxy]ethylamide are obtained in an analogous manner to that described in Example 13.

EXAMPLE 15

Manufacture of 1000 capsules with 260 mg of the active ingredients per capsule:

| Composition: | |
| --- | --- |
| rifampicin | 250 g |
| N—acetylmuramyl-L-alanyl-D-isoglutamine 2-[(3′R)-hydroxy(2′S)-palmitoylaminooctadecyloxyhydroxyphosphoryloxy]ethylamide | 10 g |
| talcum | 36 g |
| wheat starch | 24 g |
| magnesium stearate | 16 g |
| lactose | 4 g |
| | 340 g |

Preparation

The pulverulent substances are forced through a sieve having a mesh width of 0.6 mm and thoroughly mixed. Gelatin capsules are prepared by a capsule-filling machine with 340 g of this mixture per capsule.

EXAMPLE 16

Manufacture of 1000 capsules containing 105 mg of the active substances per capsule:

| Composition: | |
| --- | --- |
| rifampicin | 100 g |
| N—acetyldesmethylmuramyl-L-alanyl-D-isoglutamine 2-(hexadecyloxyhydroxyphosphoryloxy)ethylamide | 5 g |
| ethyl cellulose | 3 g |
| stearic acid | 3 g |
| | 111 g |

Preparation

The ethyl cellulose and the stearic acid are dissolved in 120 ml of methylene chloride, the antibiotic is added and the composition is forced through a sieve having a mesh width of 0.6 mm at a temperature of approximately 40°, the methylene chloride evaporating. 156 mg of the resulting granulate are filled into 0.5 ml gelatin capsules by means of a capsule-filling machine.

EXAMPLE 17

Manufacture of foodstuff containing 0.005% of the active substances:

| Pre-mixture: | |
| --- | --- |
| rifampicin or chlorotetracycline | 30 g |
| N—acetyldesmethylmuramyl-L-alanyl-D-isoglutaminyl-L-alanine 2-(hexadecyloxyhydroxyphosphoryloxy)ethylamide | 10 g |
| powdered sugar | 50 g |

-continued

Pre-mixture:

| | |
|---|---|
| soya bean foodstuff (extracted with solvents) | 275 g |
| | 365 g |

Additives

| | |
|---|---|
| cornflour | 500.0 kg |
| soya bean flour, 44% protein | 300.0 kg |
| alfalfa flour | 13.5 kg |
| dicalcium phosphate | 18.0 kg |
| calcium carbonate (ground) | 4.5 kg |
| salt | 2.3 kg |
| fish meal, 60% protein | 18.0 kg |
| stab. fat | 27.0 kg |
| dry whey residue | 18.0 kg |
| manganese sulphate | 0.2 kg |
| zinc oxide | 1.3 kg |
| d,l-methionine | 0.7 kg |
| vitamin premixture | 4.5 kg |
| | 908.0 kg |

The vitamin premixture contains in 4.5 kg: 16 000 000 I.U. vit.A, 1 000 000 I.U. vit.D$_3$, 5 000 I.U. vit.E acetate, 6 g vit.K$_3$, 6 mg vit.B$_{12}$, 3 g of riboflavin, 30 g of niacin, 5 g of calcium pantothenate and 100 g of ethoxyquin (1,2-dihydro-6-ethoxy-2,2,4-trimethylquinoline), and cornflour to make up the 4.5 kg.

Method of production

The active substances and sugar are thoroughly mixed with each other, forced through a sieve having a mesh width of 0.6 mm and then mixed with the soya bean flour. The premixture is then added to the foodstuff in the amount corresponding to the desired concentration, and homogenised in a horizontal drum mixer.

EXAMPLE 18

In an analogous manner to those described in Examples 15 and 16, combination preparations are obtained which, in addition to the adjuncts and carriers, contain per capsule the following active ingredients in the quantities specified:

(a) 500 mg of cephalexin and 5 mg of N-acetylmuramyl-L-alanyl-D-isoglutaminyloxymethylcarboxylic acid 2-(hexadecyloxyhydroxyphosphoryloxy)ethylamide, (b) 750 mg of ampicillin and 40 mg of N-acetyldesmethylmuramyl-L-alanyl-D-isoglutamine 2-(cholest-5-ene-3β-oxyhydroxyphosphoryloxy)ethylamide, (c) 100 mg of doxycycline and 15 mg of N-acetylmuramyl-L-valyl-D-isoglutamine 2-(tetradecyloxyhydroxyphosphoryloxy)ethylamide, (d) 300 mg of methacycline and 15 mg of N-benzoyldesmethylmuramyl-L-seryl-D-isoglutamine 2-(hexadecyloxyhydroxyphosphoryloxy)ethylamide, (e) 250 mg of erythromycin estolate and 30 mg of N-propionyldesmethylmuramyl-N-methylalanylisoglutamine 2-(cholest-5-ene-3β-oxyhydroxyphosphoryloxy)ethylamide.

EXAMPLE 19

Manufacture of a sterile dry substance for injection (lyophilisation).

500 mg of cefsulodin and 10 mg of N-acetylmuramyl-L-α-aminobutyryl-D-isoglutamine 2-(tetradecyloxyhydroxyphosphoryloxy)ethylamide are dissolved in 5 ml of water while stirring. The solution is sterile-filtered and filled under aseptic conditions into a sterile ampoule glass (phial) and lyophilised. The dry substance can be used for parenteral administration after dissolving in water or physiological solutions.

EXAMPLE 20

Manufacture of a sterile dry substance for injection (powder filling).

500 mg of sterile cefsulodin and 15 mg of sterile N-propionyldesmethylmuramyl-L-alanyl-D-isoglutamine 2-(hexadecyloxyhydroxyphosphoryloxy)ethylamide are homogeneously mixed and filled into an ampoule glass under aseptic conditions. The dry substance can be used for parenteral administration after dissolving in water or physiological solutions.

What is claimed is:

1. Pharmaceutical preparation with antiobiotic activity for parenteral or enteral administration which contains an antibiotically effective combination of at least one antibiotic and an amount sufficient to enhance the activity of said antibiotic of at least one phosphorylmuramyl peptide of the formula

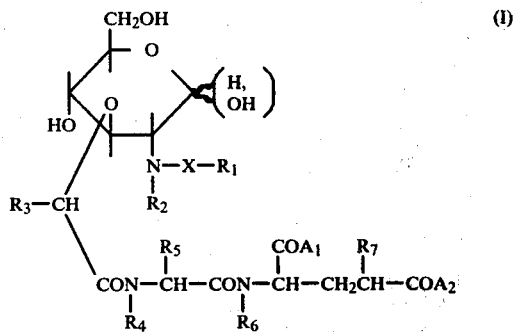

(I)

wherein X represents carbonyl, $R_1$ represents lower alkyl unsubstituted or substituted by hydroxy, lower alkoxy or halogen, or represents phenyl unsubstituted or substituted by hydroxy, lower alkoxy, lower alkyl or halogen, $R_2$, $R_4$ or $R_6$ independently of one another represent hydrogen or lower alkyl, $R_3$ represents hydrogen or lower alkyl, $R_5$ represents hydrogen, lower alkyl having from 1 to 3 carbon atoms unsubstituted or substituted by hydroxy, lower alkoxy, mercapto, lower alkylthio, amino or halogen, or represents cycloalkyl or cycloalkyl-lower alkyl in which the lower alkyl radical contains from 1 to 3 carbon atoms, and in each of which the cycloalkyl radical contains from 4 to 6 carbon atoms, phenyl or phenyl-lower alkyl having from 1 to 3 carbon atoms in the lower alkyl radical and each unsubstituted or substituted by hydroxy, lower alkoxy or halogen, or heterocyclyl or heterocyclyl-lower alkyl having from 1 to 3 carbon atoms in the lower alkyl radical, and each containing one or two nitrogen atoms and having 5 or 6 ring members, or $R_4$ and $R_5$ together alternatively represent alkylene having 3 to 4 carbon atoms, $R_7$ represents hydrogen, and one of the radicals $A_1$ and $A_2$ represents a radical of the formula

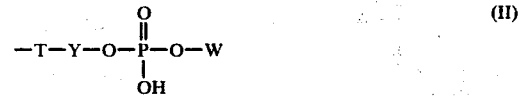

(II)

in which T represents HN or O, Y represents lower alkylene which is unsubstituted or substituted by hydroxy, lower alkoxy, lower alkanoyloxy, halogen, mercapto, lower alkylthio, lower alkanoylthio, amino-lower alkyl, mono- or di- lower alkylamino-lower alkyl, lower alkanoylamino-lower alkyl, aminocarbonyl, lower alkyl, cycloalkyl having 5 or 6 carbon atoms, a phenyl or a phenyl-lower alkyl radical, or by heterocyclyl or heterocyclyl-lower alkyl having from 1 to 3 carbon atoms in the lower alkyl radical and each containing one or two nitrogen atoms and having 5 or 6 ring members or a radical of one of the formulae

$Y_1-COO-Y_2$ (IIIa)

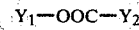

$Y_1-OOC-Y_2$ (IIIb)

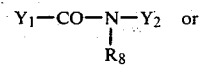

$Y_1-CO-N-Y_2$ or (IIIc)
$\quad\quad\quad\;\;|$
$\quad\quad\quad\;R_8$

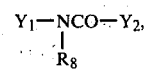

$Y_1-NCO-Y_2,$ (IIId)
$\quad\;\;|$
$\quad\;R_8$ in which $Y_1$ and $Y_2$ each represents lower alkylene which is unsubstituted or substituted by hydroxy, lower alkoxy, lower alkanoyloxy, halogen, mercapto, lower alkylthio, lower alkanoylthio, amino-lower alkyl, mono- or di-lower alkylamino-lower alkyl, lower alkanoylamino-lower alkyl, aminocarbonyl, lower alkyl, cycloalkyl having 5 or 6 carbon atoms, a phenyl or a phenyl-lower alkyl radical, or by heterocyclyl or heterocyclyl-lower alkyl having from 1 to 3 carbon atoms in the lower alkyl radical and each containing one or two nitrogen atoms and having 5 or 6 ring members and $R_8$ represents hydrogen, W represents an alkyl or alkenyl group having from 7 to 30 carbon atoms which is unsubstituted or substituted by hydroxy, lower alkoxy, lower alkanoyloxy, halogen, amino, lower alkylamino, lower alkanoylamino or oxo or represents a cycloalkyl or cycloalkenyl radical having from 10 to 30 carbon atoms which is unsubstituted or substituted by one or more alkyl radicals having from 1 to 8 carbon atoms, and the other of the radicals $A_1$ and $A_2$ represents hydroxy, lower alkoxy, amino or lower alkylamino, or represents aminocarbonyl-lower alkylamino unsubstituted or substituted in the lower alkyl radical by hydroxy, carboxy or amino groups, or a pharmaceutically acceptable salt thereof together with a significant amount of a pharmaceutically acceptable carrier.

2. Pharmaceutical preparation according to claim 1, which contains a compound of formula I, wherein X represents carbonyl, $R_1$ represents lower alkyl having from 1 to 7 carbon atoms or phenyl, $R_2$, $R_4$, $R_6$ and $R_7$ represent hydrogen, $R_3$ represents hydrogen or lower alkyl, $R_5$ represents hydrogen, lower alkyl, hydroxymethyl, mercaptomethyl, 1-hydroxyethyl, 2-methylthioethyl, phenylmethyl, p-hydroxyphenylmethyl, 4-aminobutyl, 4-imidazolylmethyl, or 3-indolylmethyl, or $R_4$ and $R_5$ together alternatively represent trimethylene, in which $A_1$ represents hydroxy, lower alkoxy, amino, lower alkylamino, or aminocarbonyl-lower alkylamino and $A_2$ represents a radical of the formula

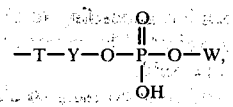

$\quad\quad\quad\;\;O$ (II)
$\quad\quad\quad\;\;\|$
$-T-Y-O-P-O-W,$
$\quad\quad\quad\quad\;|$
$\quad\quad\quad\quad OH$ in which T represents NH or O and W represents an alkyl or alkenyl group that is unsubstituted or substituted by hydroxy, lower alkoxy, lower alkanoyloxy, amino, lower alkylamino or lower alkanoylamino having up to 25 carbon atoms, or represents a cycloalkyl or cycloalkenyl radical having from 10 to 30 carbon atoms, Y represents ethylene or a radical of the formula

$Y_1-COO-Y_2$ (IIIa)

or

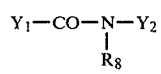

$Y_1-CO-N-Y_2$ (IIIc)
$\quad\quad\quad\;\;|$
$\quad\quad\quad\;R_8$ in which $R_8$ represents hydrogen and $Y_1$ and $Y_2$, independently of one another, each represents lower alkylene having from 1 to 7 carbon atoms whichh is optionally substituted by hydroxy, lower alkoxy, mercapto, methylthio, phenyl, 4-imidazolyl or 3-indolyl, or a pharmaceutically acceptable salt thereof.

3. Pharmaceutical preparation according to claim 1, which contains a compound of formula I, wherein X represents carbonyl, $R_1$ represents lower alkyl having from 1 to 3 carbon atoms, $R_2$, $R_4$, $R_6$ and $R_7$ represent hydrogen, $R_3$ represents hydrogen or methyl, $R_5$ represents hydrogen or lower alkyl, $A_1$ represents amino and $A_2$ represents a radical of the formula

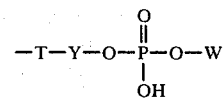

$\quad\quad\quad\;\;O$ (II)
$\quad\quad\quad\;\;\|$
$-T-Y-O-P-O-W$
$\quad\quad\quad\quad\;|$
$\quad\quad\quad\quad OH$ in which T represents NH, W represents an alkyl or alkenyl group having from 10 to 25 carbon atoms that is unsubstituted or substituted by hydroxy, lower alkoxy, lower alkanoyloxy, amino, lower alkylamino or lower alkanoylamino having up to 25 carbon atoms, or represents a cholesteryl radical, and Y represents ethylene or a radical of the formula

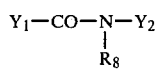

$Y_1-CO-N-Y_2$ (IIIc)
$\quad\quad\quad\;\;|$
$\quad\quad\quad\;R_8$ in which $R_8$ represents hydrogen and $Y_1$ and $Y_2$, independently of one another, each represents lower alkylene, or a pharmaceutically acceptable salt thereof.

4. Pharmaceutical preparation according to claim 2 or 3, which contains a compound of the formula I wherein the meanings for $A_1$ and $A_2$ are interchanged, or a pharmaceutically acceptable salt thereof.

5. Pharmaceutical preparation according to claim 1, which contains a compound of the formula I, wherein X represents carbonyl, $R_1$ represents lower alkyl having from 1 to 3 carbon atoms or phenyl, $R_2$, $R_4$ and $R_6$ represent hydrogen, $R_3$ represents hydrogen or lower alkyl having from 1 to 3 carbon atoms, $R_5$ represents hydrogen, lower alkyl having from 1 to 3 carbon atooms unsubstituted or substituted by hydroxy, methoxy, mercapto, methylthio or halogen, or represents phenyl or phenylmethyl each unsubstituted or substituted by hydroxy, methoxy or halogen, or represents heterocyclyl or heterocyclylmethyl each containing one or two nitrogen atoms and having 5 ring members, or $R_4$ and $R_5$ together alternatively represent trimethylene, $R_7$ represents hydrogen and one of the radicals $A_1$ and $A_2$ represents a radical of the formula

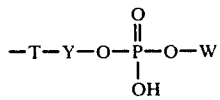   (II)

in which T represents HN or O, Y represents lower alkylene having 2 or 3 carbon atoms, or a radical of the formula (IIIa) or (IIIc)

   (IIIa)

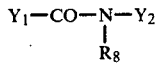   (IIIc)

in which $R_8$ represents hydrogen, and $Y_1$ and $Y_2$, independently of one another, each represents lower alkylene having from 1 to 3 carbon atoms unsubstituted or substituted by hydroxy, lower alkoxy, mercapto or lower alkylthio, or lower alkylene having from 1 to 3 carbon atoms that is unsubstituted or substituted by hydroxy-, methoxy- or halogen-substituted phenyl or phenyl-lower alkyl or by heterocyclyl or heterocyclyl-lower alkyl having from 1 to 3 carbon atoms in the lower alkyl radical and each containing one or two nitrogen atoms and having 5 or 6 ring members, W represents an alkyl group having from 10 to 25 carbon atoms substituted in the 2-position by hydroxy, lower alkanoyloxy, amino or lower alkanoylamino, and the other of the radicals $A_1$ and $A_2$ represents hydroxy, lower alkoxy, amino, lower alkylamino or aminocarbonyl-lower alkylamino, or a pharmaceutically acceptable salt thereof.

6. Pharmaceutical preparation according to claim 1, which contains a compound of the formula I, wherein $R_1$ represents lower alkyl or a pharmaceutically acceptable salt thereof.

7. Pharmaceutical preparation according to claim 1, which contains a compound of the formula I, wherein $R_4$ represents alkyl having from 1 to 4 carbon atoms and $R_2$ and $R_6$ represent hydrogen or a pharmaceutically acceptable salt thereof.

8. Pharmaceutical preparation according to claim 1, which contains N-acetyldesmethylmuramyl-L-alanyl-D-isoglutaminyl-L-alanine 2-(hexadecyloxyhydroxyphosphoryloxy)ethylamide or a pharmaceutically acceptable salt thereof.

9. Pharmaceutical preparation according to claim 1, which contains N-acetylmuramyl-L-alanyl-D-isoglutaminyl-L-alanine 2-(hexadecyloxyhydroxyphosphoryloxy)ethylamide or a pharmaceutically acceptable salt thereof.

10. Pharmaceutical preparation according to claim 1, which contains N-acetylmuramyl-L-alanyl-D-isoglutaminyl-L-alanine 2-(tetradecyloxyhydroxyphosphoryloxy)ethylamide or a pharmaceutically acceptable salt thereof.

11. Pharmaceutical preparation according to claim 1, which contains N-acetylmuramyl-L-alanyl-D-isoglutaminyl-L-alanine 2-[(3′R)-hydroxy-(2′S)-palmitoylamino-4′t-octadecenyloxyhydroxyphosphoryloxy]ethylamide or a pharmaceutically acceptable salt thereof.

12. Pharmaceutical preparation according to claim 1, which contains N-acetylmuramyl-L-α-aminobutyryl-D-isoglutaminyl-L-alanine 2-[(3′R)-hydroxy-(2′S)-palmitoylamino-4′t-octadecenyloxyhydroxyphoryloxy]ethylamide or a pharmaceutically acceptable salt thereof.

13. Pharmaceutical preparation according to claim 1, which contains N-acetylmuramyl-L-α-aminobutyryl-D-isoglutaminyl-L-alanine 2-[(3′R)-hydroxy-(2′S)-palmitoylamino-octadecyloxyhydroxyphosphoryloxy]ethylamide or a pharmaceutically acceptable salt thereof.

14. Pharmaceutical preparation according to claim 1, which contains N-acetylmuramyl-L-alanyl-D-isoglutaminyl-L-alanine 2-(cholest-5-ene-3β-oxy-hydroxyphosphoryloxy)ethylamide or a pharmaceutically acceptable salt thereof.

15. Pharmaceutical preparation according to claim 1, which contains N-benzoylmuramyl-L-alanyl-D-isoglutaminyl-L-alanine 2-(hexadecyloxyhydroxyphosphoryloxy)ethylamide or a pharmaceutically acceptable salt thereof.

16. Pharmaceutical preparation according to claim 1, which contains a compound selected from the group consisting of N-acetylmuramyl-L-alanyl-D-isoglutamine 2-(hexadecyloxyhydroxyphosphoryloxy)ethylamide, N-acetyldesmethylmuramyl-L-alanyl-D-isoglutamine 2-(hexadecyloxyhydroxyphosphoryloxy)ethylamide, N-acetylmuramyl-L-alanyl-D-isoglutaminyloxymethylcarboxylic acid 2-(hexadecyloxyhydroxyphosphoryloxy)ethylamide, N-acetylmuramyl-L-alanyl-D-isoglutamine 2-[(3′-R)-hydroxy-(2′S)-palmitoylamino-4′t-octadecenyloxyhydroxyphosphoryloxy]ethylamide, N-acetyldesmethylmuramyl-L-alanyl-D-isoglutamine 2-[(3′R)-hydroxy-(2′S)-palmitoylamino-4′t-octadecenyloxyhydroxyphosphoryloxy]ethylamide, N-acetyldesmethylmuramyl-L-alanyl-D-isoglutaminyl-L-alanine 2-[(3′-R)-hydroxy-(2′-S)-palmitoylamino-4′t-octadecenyloxyhydroxyphosphoryloxy]ethylamide, N-acetylmuramyl-L-alanyl-D-isoglutaminyloxymethylcarboxylic acid [(3′R)-hydroxy-(2′S)-palmitoylamino-4′t-octadecenyloxyhydroxyphosphoryloxy]ethylamide or a pharmaceutically acceptable salt thereof.

17. Pharmaceutical preparation according to claim 1, which contains an antibiotic selected from β-lactam antibiotics, aminoglycosides, tetracyclines, macrolides, lincomycins, polyene antibiotics, polypeptide antibiotics, anthracyclines, chloramphenicols, thiamphenicols, cycloserines, fusidic acids or rifamycins.

18. Pharmaceutical preparation according to claim 1, which contains an antibiotic selected from amoxycillin, ampicillin, carbenicillin, cloxacillin, cyclacillin, dicloxacillin, mecillinam, methicillin, penicillin G, penicillin V, pivampicillin, sulbenicillin, azlocillin, ticarcillin, mezlocillin, pivmecillinam and 6-(4-endoazatricyclo[5.2.2.0$^{2,6}$]undec-8-enyl)-methyleneaminopencillanic acid.

19. Pharmaceutical preparation according to claim 1, which contains an antibiotic selected from cefaclor, cefazaflur, cefazolin, cefadroxil, cefoxitin, cefuroxim, cephacetril, cephalexin, cephaloglycin, cephaloridines, cephalotin, cefamandol, cephanon, cephapirin, cefatrizin, cephradin, cefroxadin (7β-[D-2-amino-2-(1,4-cyclohexadienyl)-acetamido]-3-methoxy-3-cephem-4-carboxylic acid), cefsulodin, cefotaxim, cefotiam, ceftezol and cefazedon.

20. Pharmaceutical preparation according to claim 1, which contains an antibiotic selected from nocardicine A, thienamycin and clavulanic acid.

21. Pharmaceutical preparation according to claim 1, which contains an antibiotic selected from streptomycin, streptomycin A, neomycin B, tobramycin, dibekacin, kanamycins, amicacins, gentamycins, sisomicin, netilmicin, lividomycin, ribocamycin and paromomycin.

22. Pharmaceutical preparation according to claim 1, which contains an antibiotic selected from tetracycline, doxycycline, chlorotetracycline, oxytetracycline and methacycline.

23. Pharmaceutical preparation according to claim 1, which contains an antibiotic selected from maridomycin, spiramycins, erythromycins, oleandomycins and lincomycins.

24. Pharmaceutical preparation according to claim 1, which contains an antibiotic selected from amphotericin B, its methyl esters and nystalin.

25. Pharmaceutical preparation according to claim 1, which contains an antibiotic selected from colistin, gramicidin S, polymyxin B, virginamycin, tyrothricin, viomycin and vancomycin.

26. Pharmaceutical preparation according to claim 1, which contains an antibiotic selected from rifamycin S, rifamycin SV, rifamycin B and rifampicin.

27. A process for increasing the activity of antibiotics comprising administering to animals in need of such administration a pharmaceutical preparation according to one of claims 1–26 wherein the muramyl peptide is administered up to 24 hours before or after the antibiotic.

* * * * *